(12) United States Patent
Shiraishi et al.

(10) Patent No.: US 10,052,015 B2
(45) Date of Patent: Aug. 21, 2018

(54) ENDOSCOPE SYSTEM, PROCESSOR DEVICE, AND METHOD FOR OPERATING ENDOSCOPE SYSTEM

(71) Applicant: FUJIFILM Corporation, Tokyo (JP)

(72) Inventors: Yasushi Shiraishi, Ashigarakami-gun (JP); Tatsuya Aoyama, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 338 days.

(21) Appl. No.: 14/869,062

(22) Filed: Sep. 29, 2015

(65) Prior Publication Data

US 2016/0089011 A1    Mar. 31, 2016

(30) Foreign Application Priority Data

Sep. 30, 2014   (JP) ................................. 2014-202648
Sep. 30, 2014   (JP) ................................. 2014-202649

(51) Int. Cl.
*A61B 1/06*   (2006.01)
*G06K 9/46*   (2006.01)
(Continued)

(52) U.S. Cl.
CPC ........ *A61B 1/0638* (2013.01); *A61B 1/00009* (2013.01); *A61B 1/04* (2013.01); *A61B 1/0684* (2013.01); *G06K 9/46* (2013.01); *G06T 7/0012* (2013.01); *G06T 2207/10024* (2013.01); *G06T 2207/10068* (2013.01); *G06T 2207/10152* (2013.01); *G06T 2207/20212* (2013.01); *G06T 2207/30101* (2013.01); *H04N 5/2354* (2013.01); *H04N 9/045* (2013.01); *H04N 2005/2255* (2013.01)

(58) Field of Classification Search
CPC .................................................. A61B 1/0638
See application file for complete search history.

(56) References Cited

U.S. PATENT DOCUMENTS

2006/0228004 A1   10/2006 Sato
2009/0074269 A1*   3/2009 Nishimura ............... A61B 1/04
                                            382/128
(Continued)

FOREIGN PATENT DOCUMENTS

JP   2006-252034 A   9/2006
JP   2011-110230 A   6/2011
(Continued)

OTHER PUBLICATIONS

Japanese Office Action and English translation thereof, dated May 24, 2017, for Japanese Application No. 2014-202649.

(Continued)

*Primary Examiner* — James Pontius
(74) *Attorney, Agent, or Firm* — Birch, Stewart, Kolasch & Birch, LLP

(57) ABSTRACT

An endoscope system includes a light source unit, an image sensor, an image signal obtaining section, a vessel position signal generator, a vessel width signal generator, and a vessel image signal generator. The light source unit generates illumination light. The image sensor captures an image of an object of interest irradiated with the illumination light. The image signal obtaining section obtains an image signal, which represents the object, from the image sensor. The vessel position signal generator generates a vessel position signal, which represents the position of a blood vessel of the object, from the image signal. The vessel width signal generator generates a vessel width signal, which represents the width of the blood vessel, from the image signal. The vessel image signal generator generates a vessel image signal, which represents the blood vessel, from the vessel position signal and the vessel width signal.

17 Claims, 21 Drawing Sheets

(51) Int. Cl.
  *G06T 7/00*     (2017.01)
  *A61B 1/04*     (2006.01)
  *A61B 1/00*     (2006.01)
  *H04N 9/04*     (2006.01)
  *H04N 5/225*    (2006.01)
  *H04N 5/235*    (2006.01)

(56) References Cited

U.S. PATENT DOCUMENTS

2011/0245642 A1    10/2011  Minetoma
2012/0190922 A1*   7/2012   Kaku ............... A61B 1/00009
                                              600/109
2016/0038004 A1*   2/2016   Tanaka ............. A61B 1/00009
                                              600/371

FOREIGN PATENT DOCUMENTS

JP    2011-167349 A    9/2011
JP    2011-217798 A    11/2011
JP    2013-255808 A    12/2013
JP    5435746 B2       3/2014
WO    WO 2007/119297 A1   10/2007

OTHER PUBLICATIONS

Osareh et al. "An Automated Tracking Approach for Extraction of Retinal Vasculature in Fundus Images", J. Ophthalmic Vis Res. Jan. 2010, 5(1), pp. 20-26.

* cited by examiner

ENDOSCOPE SYSTEM, PROCESSOR DEVICE, AND METHOD FOR OPERATING ENDOSCOPE SYSTEM

CROSS-REFERENCE TO RELATED APPLICATIONS

The present application claims priority under 35 U.S.C. § 119 to Japanese Patent Application No. 2014-202648, filed Sep. 30, 2014 and Japanese Patent Application No. 2014-202649, filed Sep. 30, 2014. Each of the above application(s) is hereby expressly incorporated by reference, in its entirety, into the present application.

BACKGROUND OF THE INVENTION

1. Field of the Invention

The present invention relates to an endoscope system for extracting blood vessels of an object of interest from an image signal obtained by imaging the object of interest, a processor device, and a method for operating an endoscope system.

2. Description Related to the Prior Art

In medical fields, diagnoses using endoscope systems are widely performed. The endoscope system comprises a light source device, an endoscope system, and a processor device. To perform diagnostic endoscopy using the endoscope system, an insertion section of the endoscope is inserted into a body cavity and illumination light is applied to an object of interest (hereinafter referred to as the object) through a distal portion of the insertion section. An image sensor provided in the distal portion captures an image of the object irradiated with the illumination light and generates image signals. An image of the object is produced from the image signals, and displayed on a monitor.

The shape and the distribution of blood vessels are important in diagnoses using the endoscope system. The endoscope systems that extract the blood vessels from the image signals through various methods have been known recently. For example, an endoscope system that extracts the blood vessels through pattern matching has been known (see US2012/0190922 (corresponding to Japanese Pat. No. 05435746) and Japanese Patent Unexamined Publication No. 2013-255808). Also, methods for extracting blood vessels with the use of a Gabor filter, a neural network, or the like have been known (see An Automated Tracking Approach for Extraction of Retinal Vasculature in Fundus Images, A. Osareh et al., J Ophthalmic Vis Res 2010; 5(1): 20-26).

Recently, it has been known that information (e.g. the density of blood vessels or the like) that is obtained based on the correct measurement of both the position and the size of the blood vessels, in addition to the detection of the presence or absence of the blood vessels, is useful for staging of a disease (e.g. the staging of cancer or the like). For example, it has been known that the blood vessel density increases with the progression of the superficial cancer of digestive tract such as Barrett's adenocarcinoma. For this reason, it has been considered that the staging accuracy is improved by using the blood vessel density. A conventional method for extracting blood vessels with an endoscope system may extract the position of the blood vessels accurately but cannot provide correct widths of the blood vessels. Therefore the conventional method cannot correctly calculate the information such as the blood vessel density or the like.

SUMMARY OF THE INVENTION

An object of the present invention is to provide an endoscope system that accurately extracts the position and the width of a blood vessel to allow correct diagnosis based on the density of the blood vessels or the like, a processor device, and a method for operating an endoscope system.

In order to achieve the above and other objects, an aspect of the present invention provides an endoscope system comprising a light source unit, an image sensor, an image signal obtaining section, a vessel position signal generator, a vessel width signal generator, a vessel image signal generator. The light source unit generates illumination light. The image sensor images an object of interest irradiated with the illumination light. The image signal obtaining section obtains an image signal from the image sensor. The image signal represents the object. The vessel position signal generator generates a vessel position signal from the image signal. The vessel position signal represents a position of a blood vessel of the object. The vessel width signal generator generates a vessel width signal from the image signal. The vessel width signal represents a width of the blood vessel. The vessel image signal generator generates a vessel image signal from the vessel position signal and the vessel width signal. The vessel image signal represents the blood vessel.

It is preferred that the image signal obtaining section obtains a first image signal as the image signal from the image sensor. The first image signal corresponds to first illumination light of the illumination light. It is preferred that the image signal obtaining section obtains a second image signal as the image signal from the image sensor. The second image signal corresponds to second illumination light that differs in wavelength range or optical spectrum from the first illumination light. It is preferred that the vessel position signal generator generates the vessel position signal from the first image signal and the second image signal. The vessel position signal represents the position of the blood vessel of the object. The vessel width signal generator generates the vessel width signal from the first image signal or the second image signal. The vessel width signal represents the width of the blood vessel of the object.

It is preferred that the vessel image signal generator uses the vessel position signal and the vessel width signal to extract the blood vessel located in the position represented by the vessel position signal and having the width represented by the vessel width signal, to generate the vessel image signal.

It is preferred that the vessel image signal generator calculates an AND of the vessel width signal and the vessel position signal to generate the vessel image signal.

It is preferred that the endoscope system further comprises an image registration processor for correcting at least one of the first image signal and the second image signal and performs registration between the object represented by the first image signal and the object represented by the second image signal. It is preferred that the vessel position signal generator generates the vessel position signal from the first and second image signals on which the registration of the objects has been performed by the image registration processor. It is preferred that the vessel width signal generator generates the vessel width signal from the first or second image signal on which the registration has been performed by the image registration processor.

It is preferred that that the endoscope system further comprises a brightness correction processor for correcting at least one of the first image signal and the second image signal and for setting a ratio between brightness of the first image signal and brightness of the second image signal to a specific ratio. It is preferred that the vessel position signal generator generates the vessel position signal from the first and second image signals in which the brightness has been adjusted by the brightness correction processor. It is preferred that the vessel width signal generator generates the vessel width signal from the first or second image signal in which the brightness has been adjusted by the brightness correction processor.

It is preferred that the vessel width signal generator performs second-order differentiation on the image signal and generates the vessel width signal based on zero-crossing points of the image signal that has been subjected to the second-order differentiation.

It is preferred that the vessel width signal generator removes noise from the first image signal or the second image signal and performs the second-order differentiation on the first or second image signal from which the noise has been removed.

It is preferred that the vessel position signal generator performs a morphological operation on the image signal to generate the blood vessel position signal.

It is preferred that the endoscope system further comprises a first remover for removing a shadow or halation from the image signal. The shadow or halation occurs due to the illumination light. It is preferred that the vessel position signal generator generates the vessel position signal from the image signal from which the shadow or the halation has been removed. It is preferred that the vessel width signal generator generates the vessel width signal from the image signal from which the shadow or the halation has been removed.

It is preferred that the first remover uses a red image signal to remove the shadow from the image signal. The red image signal corresponds to light in a red wavelength range of the illumination light.

It is preferred that the endoscope system further comprises a second remover for removing noise that occurred due to a shadow or halation from the vessel position signal and for removing noise that occurred due to the shadow or the halation from the vessel width signal.

It is preferred that the second remover uses the image signal corresponding to a red wavelength range to remove the noise that occurred due to the shadow.

It is preferred that the endoscope system further comprises a vessel density calculator for calculating blood vessel density with the use of the vessel image signal or an image generated by using the vessel image signal.

It is preferred that the endoscope system further comprises a vessel density image signal generator for generating a vessel density image signal with the use of the blood vessel density. The vessel density image signal represents the blood vessel density.

It is preferred that an image is generated by superimposing the vessel image signal onto an image generated from the image signal.

It is preferred that the endoscope system further comprises a resolution separator for separating the image signal into two or more image signals having different resolutions. It is preferred that the vessel position signal generator generates the vessel position signal for each of the resolutions. It is preferred that the vessel width signal generator generates the vessel width signal for each of the resolutions. It is preferred that the vessel image signal generator uses the vessel position signal and the vessel width signal that have been generated for each of the resolutions to generate the vessel image signal for each of the resolutions.

An aspect of the present invention provides a processor device comprising an image signal obtaining section, a vessel position signal generator, a vessel width signal generator, and a vessel image signal generator. The image signal obtaining section obtains an image signal representing an object of interest. The vessel position signal generator generates a vessel position signal from the image signal. The vessel position signal represents a position of a blood vessel of the object. The vessel width signal generator generates a vessel width signal from the image signal. The vessel width signal represents a width of the blood vessel. The vessel image signal generator generates a vessel image signal from the vessel position signal and the vessel width signal. The vessel image signal represents the blood vessel.

An aspect of the present invention provides a method for operating an endoscope system comprising an illumination light generating step, an imaging step, an image signal obtaining step, a vessel position signal generating step, a vessel width signal generating step, and a vessel image signal generating step. In the illumination light generating step, a light source unit generates illumination light. In the imaging step, an image sensor images an object of interest irradiated with the illumination light. In the image signal obtaining step, an image signal obtaining section obtains an image signal representing the object from the image sensor. In the vessel position signal generating step, a vessel position signal generator generates a vessel position signal representing a position of a blood vessel of the object from the image signal. In the vessel width signal generating step, a vessel width signal generator generates a vessel width signal representing a width of the blood vessel of the object from the image signal. In the vessel image signal generating step, a vessel image signal generator generates a vessel image signal representing the blood vessel from the vessel position signal and the vessel width signal.

Thus, an aspect of the present invention provides an endoscope system that accurately extracts the position and the width of a blood vessel to allow correct diagnosis based on the density of the blood vessels or the like, a processor device, and a method for operating an endoscope system.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

DESCRIPTION OF THE PREFERRED EMBODIMENTS

[First Embodiment]

Figure 1:
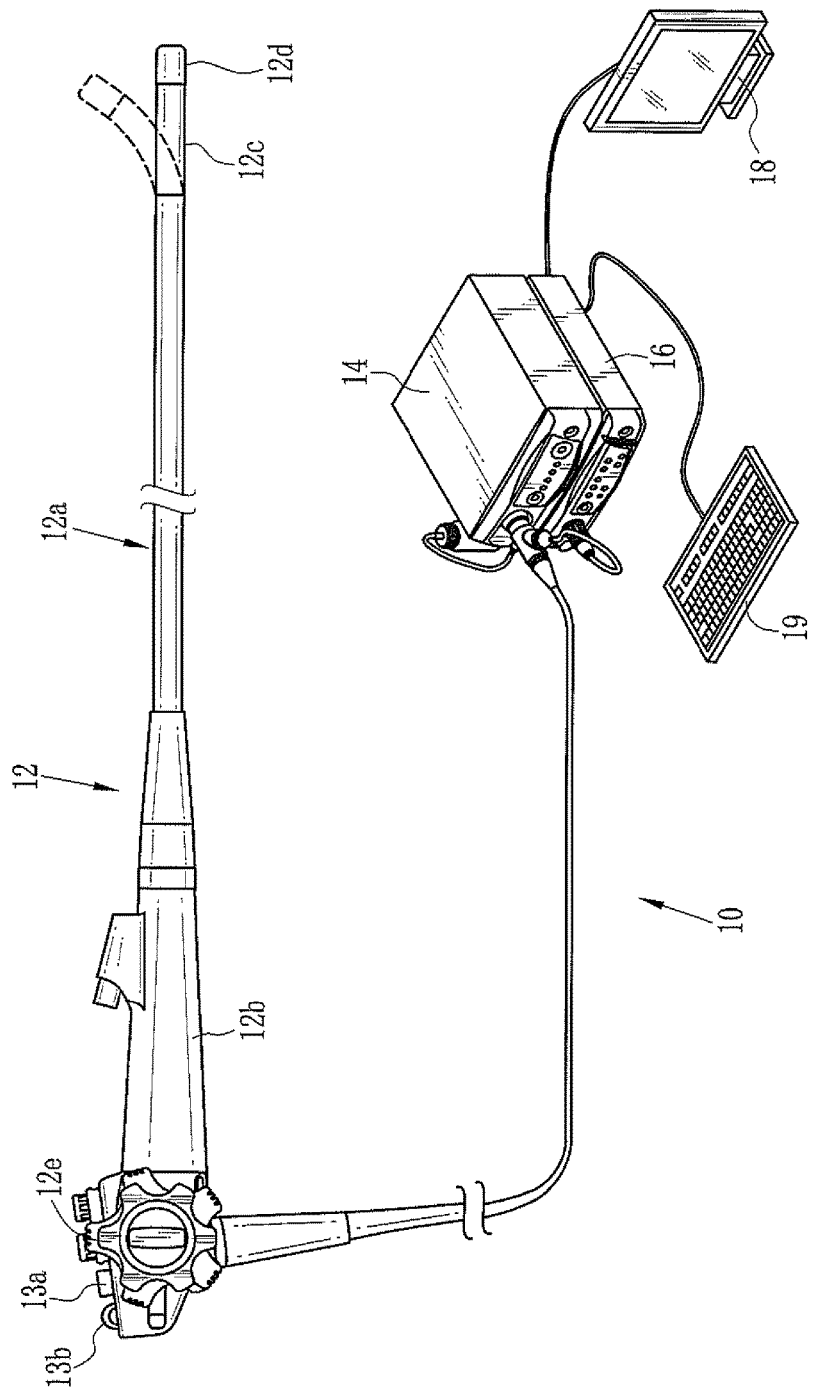
FIG. 1 is an external view illustrating an endoscope system.

In FIG. 1, an endoscope system 10 comprises an endoscope 12, a light source device 14, a processor device 16, a monitor 18, and a console 19. The endoscope 12 is connected optically to the light source device 14 and electrically to the processor device 16. The endoscope 12 comprises an insertion section 12a to be inserted into a body cavity, a control handle unit 12b provided at the proximal end of the insertion section 12a, a flexible portion 12c, and a distal portion 12d. The distal portion 12d is coupled to the flexible portion 12c, which is provided on the distal side of the insertion section 12a. The flexible portion 12c is bent by operating an angle knob 12e of the control handle unit 12b. The distal portion 12d is directed to a desired direction by bending the flexible portion 12c.

The control handle unit 12b is provided with the angle knob 12e, a mode switch (SW) 13a, a zoom operating section 13b, a still image obtaining section (not shown), and the like. The mode SW 13a is operated to switch between observation modes. The endoscope system 10 has a normal mode and a special mode as observation modes. In the normal mode, white light is used as the illumination light. A natural-colored image (hereinafter referred to as the normal image) produced by imaging an object or region of interest (hereinafter simply referred to as the object) irradiated with the white light is displayed on the monitor 18. In the special mode, a vessel image signal, in which blood vessels included in the object are extracted, is generated from an image signal obtained by imaging the object. An image (hereinafter referred to as the vessel-enhanced image) in which the blood vessels are enhanced is produced from the vessel image signal and displayed on the monitor 18.

The processor device 16 is electrically connected to the monitor 18 and the console 19. The monitor 18 outputs image(s) of the object, information associated with the corresponding image(s), and the like. The console 19 functions as a UI (user interface), which receives input operation such as setting a function. Note that an external storage unit (not shown) for recording the images and the image information may be connected to the processor device 16.

Figure 2:
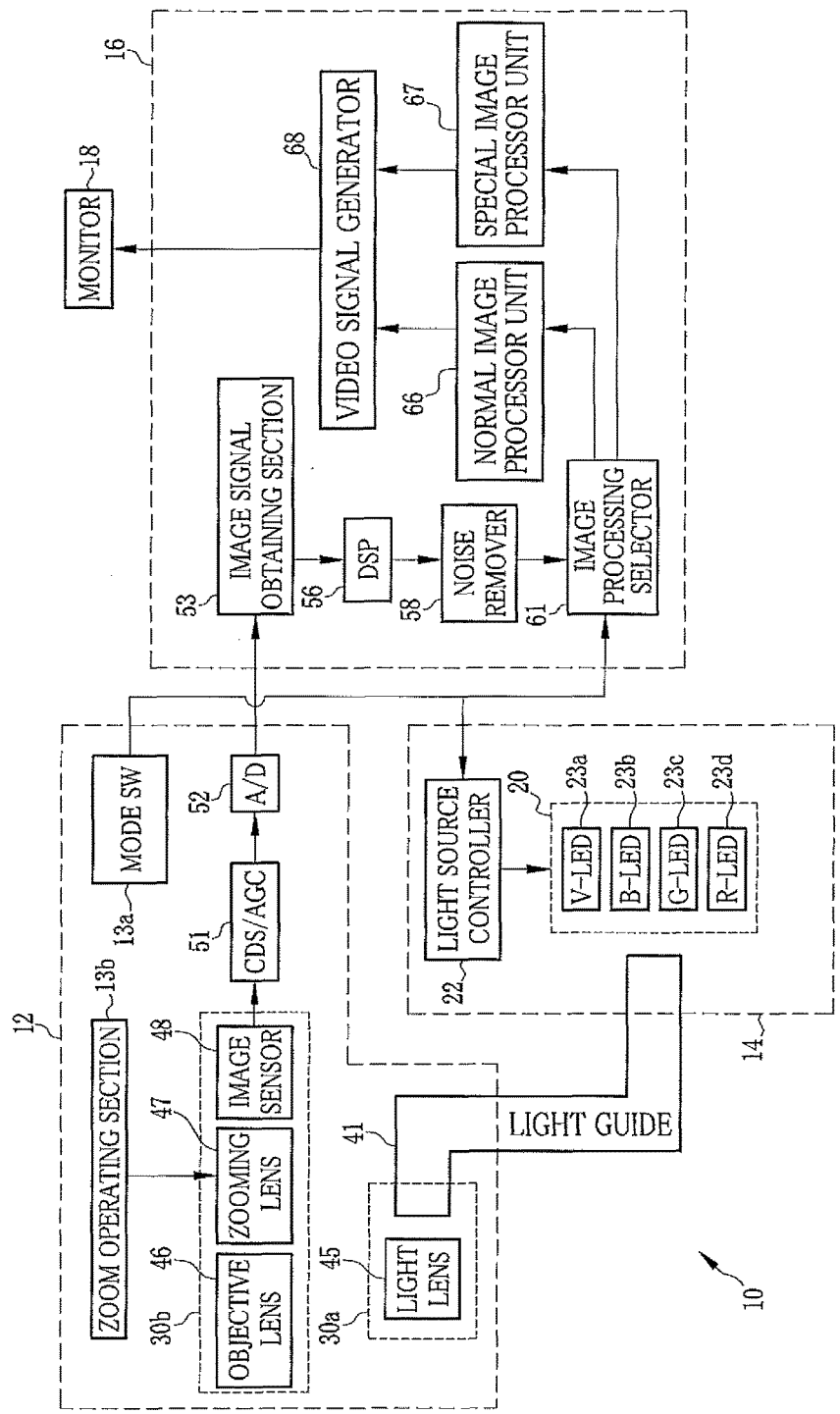
FIG. 2 is a block diagram illustrating functions of the endoscope system.
Figure 3:
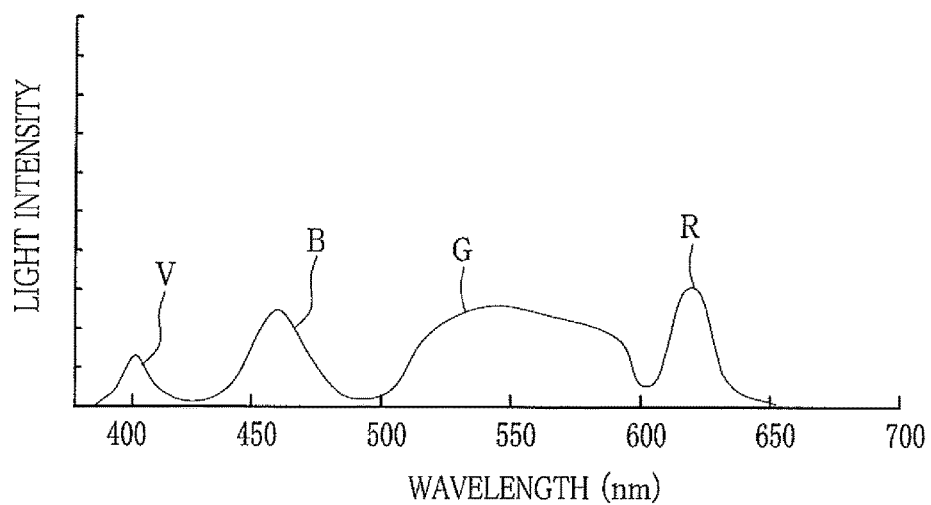
FIG. 3 is a graph illustrating optical spectrums of violet light, blue light, green light, and red light.

As illustrated in FIG. 2, the light source device 14 comprises a light source unit 20 and a light source controller 22 for controlling the light source unit 20. The light source unit 20 comprises two or more semiconductor light sources. The light source controller 22 independently turns on or off the semiconductor light sources. The light source controller 22 controls the light emission amount of each semiconductor light source to generate the illumination light to be applied to the object. In this embodiment, the light source unit 20 comprises LEDs of four colors: a V-LED (Violet Light Emitting Diode) 23a, a B-LED (Blue Light Emitting Diode) 23b, a G-LED (Green Light Emitting Diode) 23c, and an R-LED (Red Light Emitting Diode) 23d. As illustrated in FIG. 3, the V-LED 23a is a violet semiconductor light source that emits violet light V having a wavelength range of 380 to 420 nm and the center wavelength 405 nm. The B-LED 23b is a blue semiconductor light source that emits blue light B having a wavelength range of 420 to 500 nm and the center wavelength 460 nm. The G-LED 23c is a green semiconductor light source that emits green light G having a wavelength range of 480 to 600 nm. The R-LED 23d is a red semiconductor light source that emits red light R having a wavelength range of 600 to 650 nm and the center wavelength 620-630 nm. Note that each of the center wavelength of the V-LED 23a and the center wavelength of the B-LED 23b has a width in the order of ±5 nm to ±10 nm.

Turning on and off of the LEDs 23a to 23d, the light emission amounts, and the like are controlled independently by the light source controller 22 through inputting the corresponding control signals. In this embodiment, in either of the normal mode and the special mode, the light source controller 22 turns on all of the V-LED 23a, the B-LED 23b, the G-LED 23c, and the R-LED 23d. The illumination light used in the normal mode and the special mode is white light that contains the violet light V, the blue light B, the green light G, and the red light R.

The light of four colors from the respective LEDs 23a to 23d are incident on the light guide 41, which extends through the insertion section 12a, through a light path combiner (not shown) comprising a mirror, a lens, and the like. The light guide 41 extends through the endoscope 12 and a universal cord, which connects the endoscope 12 to the light source device 14 and the processor device 16. The light guide 41 transmits the illumination light, which is generated by the light source unit 20, to the distal portion 12d of the endoscope 12.

The distal portion 12d of the endoscope 12 comprises an illumination optical system 30a and an imaging optical system 30b. The illumination optical system 30a has a light lens 45. The illumination light transmitted through the light guide 41 is applied to the object through the light lens 45. The imaging optical system 30b has an objective lens 46, a zooming lens 47, and an image sensor 48. Various types of light, such as the light reflected from the object, scattered light, and/or phosphor, caused by the illumination light are incident on the image sensor 48 through the objective lens 46 and the zooming lens 47. Thereby an image of the object is formed on the image sensor 48. Note that the zooming lens 47 is moved as desired between the telephoto end and the wide angle end by operating the zoom operating section 13b, to magnify or reduce the size of the reflection image of the object formed on the image sensor 48.

Figure 4:
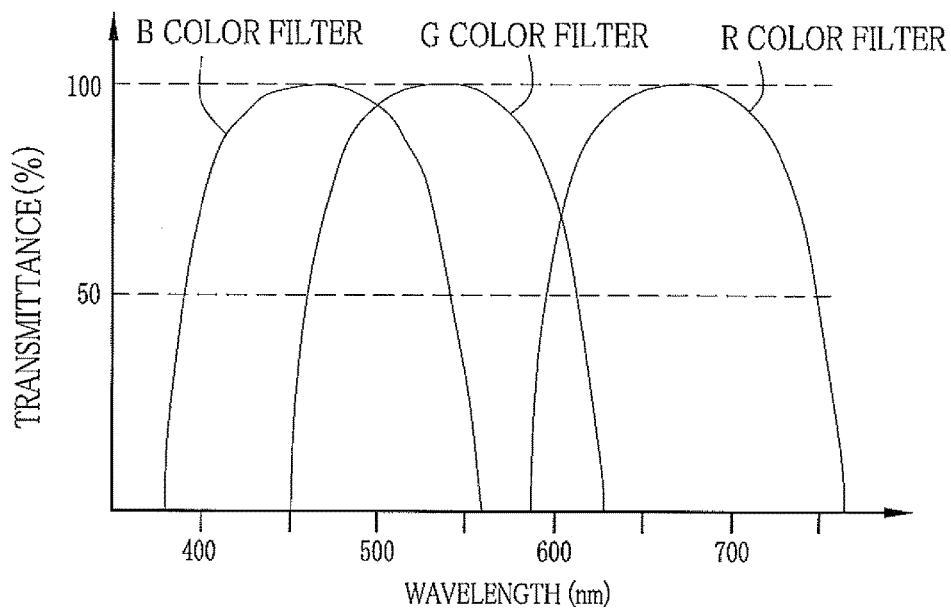
FIG. 4 is a graph illustrating spectral characteristics of color filters.

The image sensor 48 is a color image sensor for imaging an object irradiated with the illumination light. Each pixel of the image sensor 48 is provided with an R (red) color filter, a G (green) color filter, or a B (blue) color filter (see FIG. 4). The image sensor 48 comprises B pixels (blue pixels) provided with B color filters, G pixels (green pixels) provided with G color filters, and R pixels (red pixels) provided with R color filters. The B pixels receive light from violet to blue. The G pixels receive green light. The R pixels receive red light. The R pixels, the G pixels, and the B pixels output an R (red) image signal, a G (green) image signal, and a B (blue) image signal, respectively.

A CCD (Charge Coupled Device) image sensor or a CMOS (Complementary Metal-Oxide Semiconductor) image sensor is used as the image sensor 48. Instead of the image sensor 48 of primary colors, a complementary color image sensor with complementary color filters of C (cyan), M (magenta), Y (yellow), and G (green) may be used. The complementary color image sensor outputs CMYG image signals of four colors. In a case where the complementary color image sensor is used, the CMYG image signals of four colors are outputted and converted into the RGB image signals of three colors through complementary color-primary color conversion. Thereby, the RGB image signals the same as those of the image sensor 48 are generated. A monochrome image sensor with no color filters may be used instead of the image sensor 48.

The CDS/AGC circuit 51 performs correlated double sampling (CDS) and automatic gain control (AGC) on an analog image signal obtained from the image sensor 48. The image signal that has passed through the CDS/AGC circuit 51 is converted into a digital image signal by an A/D (Analog to digital) converter 52. After the A/D conversion, the digital image signal is inputted to the processor device 16.

The processor device 16 comprises an image signal obtaining section 53, a DSP (Digital Signal Processor) 56, a noise remover 58, an image processing selector 61, a normal image processor unit 66, a special image processor unit 67, and a video signal generator 68. The image signal obtaining section 53 obtains a digital image signal from the image sensor 48 through the CDS/AGC circuit 51 and the A/D converter 52.

The DSP 56 performs various types of image processing such as defect correction process, offset processing, gain correction process, linear matrix processing, gamma conversion process, demosaicing process, and the like on the image signal obtained. In the defect correction process, signals of defective pixels of the image sensor 48 are corrected. In the offset processing, dark current components are removed from the image signals that have been subjected to the defect correction process. Thereby an accurate zero level is set. In the gain correction process performed after the offset processing, a signal level is adjusted or corrected by multiplying the image signals by a specific gain.

After the gain correction process, the image signals are subjected to the linear matrix processing to increase color reproducibility. Thereafter, brightness and saturation are adjusted or corrected through the gamma conversion process. After the gamma conversion process, the demosaicing process (also referred to as equalization process or synchronization process) is performed to generate signal (s) of color (s) lacking in each pixel through interpolation. Owing to the demosaicing process, each pixel has three colors (RGB) of signals. The noise remover 58 performs a noise removal process (for example, moving average method or median filter method) on the image signal that has been subjected to the demosaicing process performed by the DSP 56. Throughout the specification, "remove" means not only to eliminate and but also to reduce something to a required or predetermined level. The image signal from which the noise has been removed is transmitted to the image processing selector 61. In a case where the observation mode is set to the normal mode by operating the mode SW 13a, the image processing selector 61 transmits the RGB image signals to the normal image processor unit 66. In a case where the observation mode is set to the special mode by operating the mode SW 13a, the image processing selector 61 transmits the RGB image signals to the special image processor unit 67.

The normal image processor unit 66 operates in a case where the observation mode is set to the normal mode, and performs a color conversion process, a color enhancement process, and a structure enhancement process on the image signals received, thereby producing the normal image. The color conversion process is performed on the RGB image signals through 3×3 matrix processing, a tone conversion process, a three-dimensional LUT process, and the like, for example. The color enhancement process is performed on the image signals that have been subjected to the color conversion process. The structure enhancement process is to enhance the structure of the object (e.g. surface blood vessels, pit patterns, or the like). The structure enhancement process is performed on the image signals that have been subjected to the color enhancement process. A color image produced from normal image signals that that have been subjected to the above-described various types of image processing all the way up to the structure enhancement process is referred to as the normal image, for example.

Figure 5:
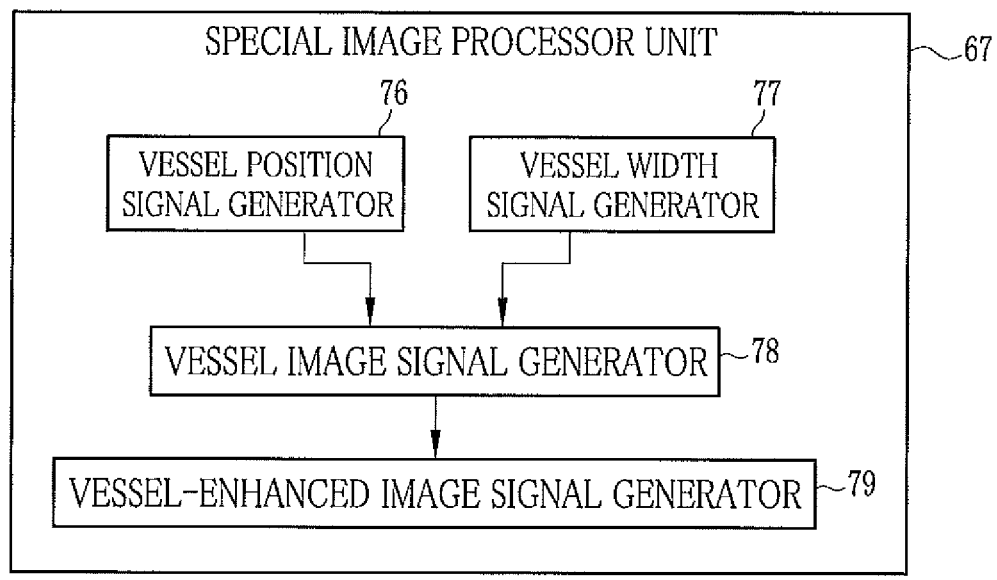
FIG. 5 is a block diagram illustrating functions of a special image processor.

The special image processor unit 67 operates in a case where the mode is set to the special mode. As shown in FIG. 5, a special image processor unit 67 comprises a vessel position signal generator 76, a vessel width signal generator 77, a vessel image signal generator 78, and a vessel-enhanced image signal generator 79.

The vessel position signal generator 76 generates a vessel position signal, which represents the position of blood vessels of the object, from the image signal received from the image processing selector 61. To be more specific, the vessel position signal generator 76 performs black-hat transform to extract the blood vessels of the object from the inputted image signal, and then binarizes the image signal that has been subjected to the black top-hat transform, to generate a vessel position signal. In the vessel position signal, each of the pixels representing the blood vessels has a pixel value of a specific positive value (for example "1") and each of the remaining pixels has a pixel value of "zero". The vessel position signal is inputted to the vessel image signal generator 78.

The black-hat transform is one of the morphological operations. The black-hat transform is to extract a pixel with a low pixel value relative to the pixel values of the adjacent pixels while noise is removed. Namely, the original image signal is subtracted from the image signal that has been subjected to closing operation. The closing operation is a process to perform erosion, which reduces a bright region, after dilation, which expands the bright region. An image signal obtained from the image sensor 48 has a pixel value proportionate to an amount of incident light from the object. The blood vessels contain a high amount of hemoglobin that is likely to absorb the illumination light, as compared with mucosa or the like. Because the pixel values corresponding to the blood vessels are low in the image signal, the blood vessels are extracted by the black top-hat transform. Since the original image signal is subtracted from the image signal that has been subjected to the closing operation, the pixel value of the pixel representing the blood vessels becomes high after the black top-hat transform.

Figure 6:
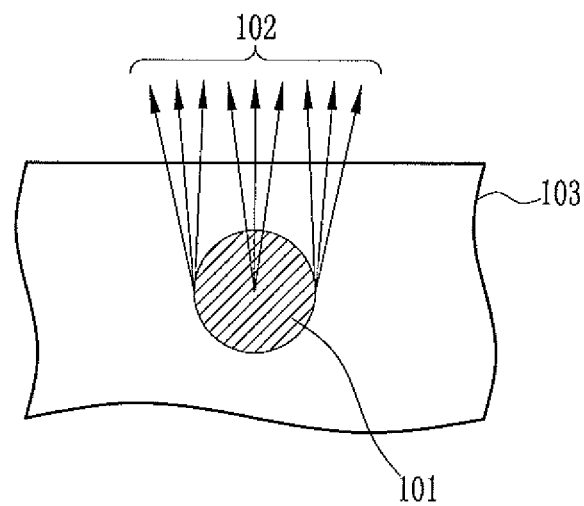
FIG. 6 is an explanatory view illustrating scattering of light reflected from blood vessels.
Figure 7:
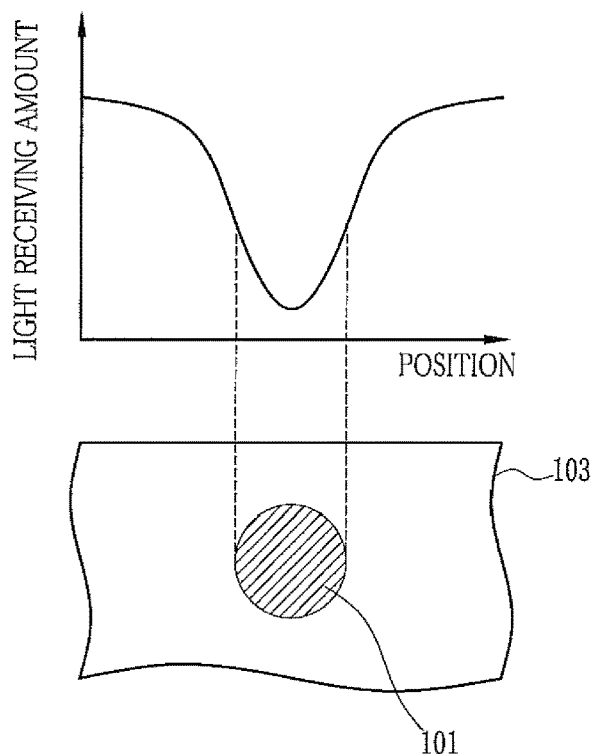
FIG. 7 is a graph illustrating distribution of the amount of light received by an image sensor.
Figure 8:
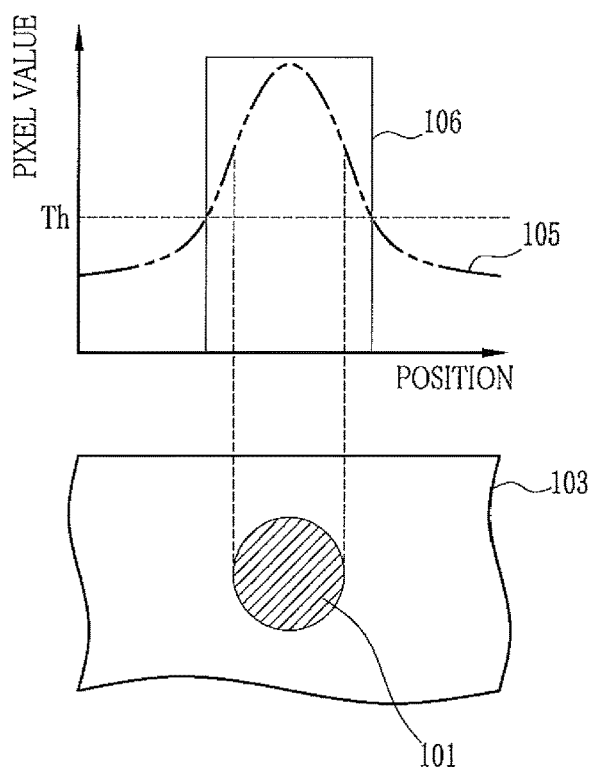
FIG. 8 is an explanatory view illustrating a method for generating a vessel position signal.

With the use of a structuring element (kernel), which is to be used for the black top-hat transform, of proper size, shape, and the like, substantially only the blood vessels are extracted accurately by the binarization of the image signal that has been subjected to the black top-hat transform. Accordingly, the vessel position signal, which is generated by the vessel position signal generator 76, accurately indicates (represents) the position of the blood vessels. However, the width (the width displayed in the image) of the blood vessel indicated by the vessel width signal is incorrect and includes an error. This is because light 102 reflected from a blood vessel 101 is diffused by scattering or the like while the light 102 is transmitted through an object 103 as shown in FIG. 6. As shown in FIG. 7, suppose the light 102 reflected from the blood vessel 101 is diffused by scattering or the like, so that the distribution of the amount of light received by the image sensor 48 has a Gaussian function shape. As shown in FIG. 8, a vessel position signal 106 is generated by the binarization of an image signal 105, which has been subjected to the black top-hat transform. In this case, the width of the blood vessel 101 in the vessel position signal 106 varies depending on a threshold value Th that is set for the binarization. Thus, the position of the blood vessel 101 indicated by the vessel position signal 106 is correct, but the width of the blood vessel 101 indicated by the vessel position signal 106 includes an error. "The position of the blood vessel 101 is correct" means that there is little noise and substantially only the blood vessel 101 is extracted.

The special image processor unit 67 receives the RGB image signals from the image processing selector 61. Note that the vessel position signal generator 76 uses at least the B image signal, which corresponds to a blue wavelength range, of the RGB image signals to generate the vessel position signal. This is because the B image signal has the highest contrast of the blood vessels in the proximity of the surface mucosal layer among the RGB image signals. The blood vessels in the surface mucosal layer are important for diagnosing a lesion or the like. In some embodiments, to detect blood vessels located at a relatively deep position in a submucosal layer, a G image signal corresponding to a green wavelength range may be used.

The vessel width signal generator 77 generate the vessel width signal, which indicates the widths of the blood vessels of the object, from the image signal received from the image processing selector 61 and inputs the vessel width signal to the vessel image signal generator 78. To be more specific, the vessel width signal generator 77 performs the black top-hat transform to extract the blood vessels of the object and then performs LoG filtering (Laplacian of Gaussian filter) on the image signal that has been subjected to the black top-hat transform. Zero-crossing points of the image signal that has been subjected to the LoG filtering are used to generate the binary vessel width signal. The LoG filter is a combination of a Gaussian filter and a Laplacian filter. The Gaussian filter smoothes the image signal and removes noise. Then the Laplacian filter performs second-order differentiation of the image signal. In other words, the vessel width signal generator 77 generates the vessel width signal, with the use of the zero-crossing points of the image signal obtained after the second-order differentiation operation.

Figure 9:
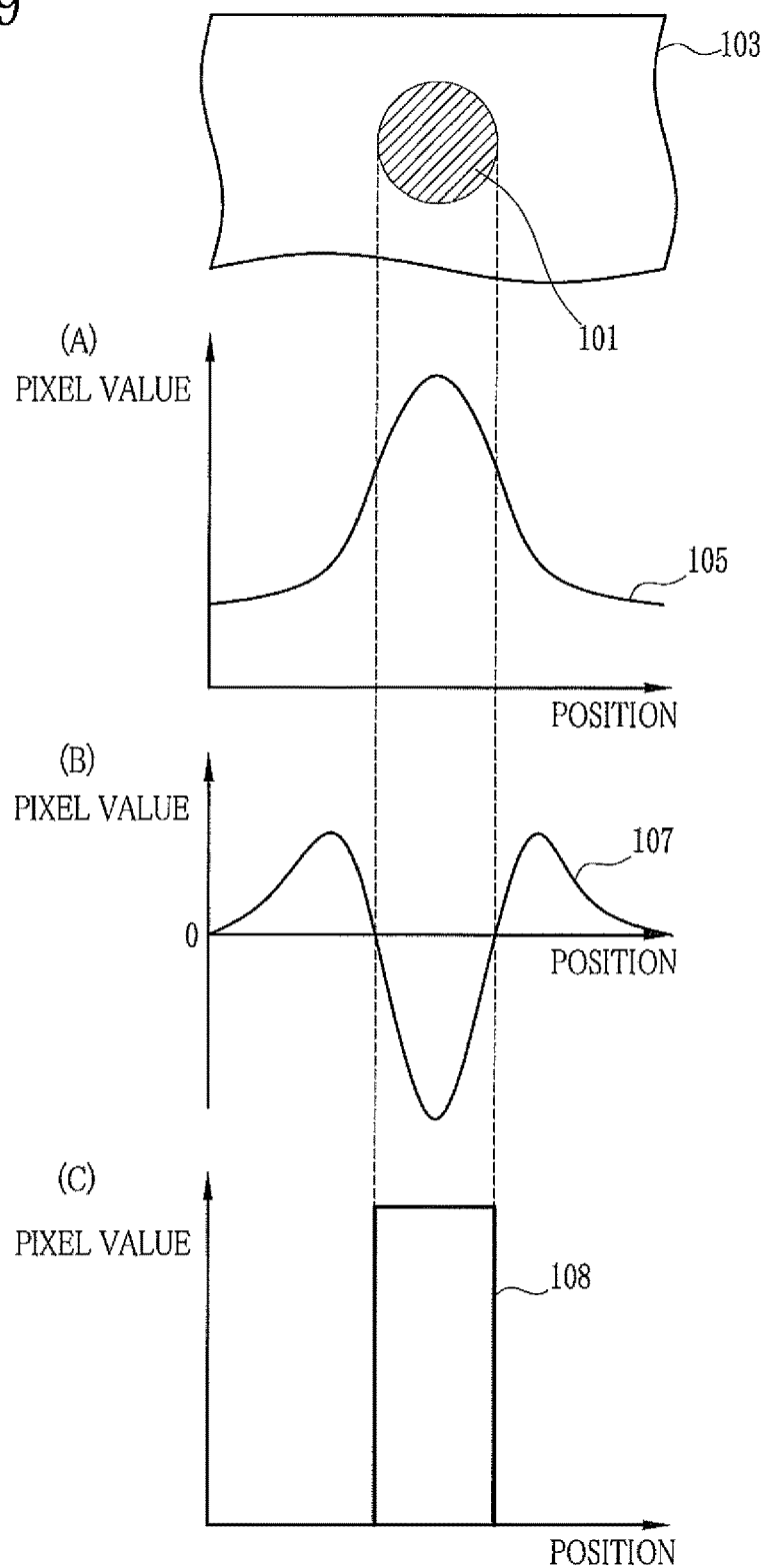
FIG. 9 is an explanatory view illustrating a method for generating a vessel width signal.

For example, Log filtering is performed on the image signal 105 (see a part (A) of FIG. 9) that has been subjected to the black top-hat transform. As illustrated in a part (B) of FIG. 9, the zero-crossing point of an image signal 107 after the LoG filtering substantially accurately indicates an edge of the blood vessel 101. As illustrated in a part (C) of FIG. 9, the vessel width signal generator 77 extracts a region between the zero-crossing points and in which a pixel value takes a negative value, from the image signal 107 that has been subjected to the LoG filtering. Thereby the vessel width signal generator 77 generates a vessel width signal 108. In the vessel width signal 108, "white" pixels having the specific positive value (for example, "1") represent a region corresponding to the blood vessels, whereas "black" pixels having the pixel value "zero" represent a region other than the blood vessels. As is obvious from the above-described method for generating the signal, the vessel width signal 108 accurately indicates the width of the blood vessel 101. However, because the Laplacian filter, which performs the differentiation, is used, extremely low noise is enhanced and an object other than the blood vessel 101 is extracted as noise. Thus, the vessel width signal 108 accurately indicates the width of the blood vessel 101 but includes the noise (that is, the positional error of the blood vessel 101).

The vessel image signal generator 78 generates the vessel image signal, which represents the blood vessels of the object, from the vessel position signal and the vessel width signal. To be more specific, the vessel image signal is generated by calculating an "AND" of the vessel position signal and the vessel width signal. Calculating the "AND" of the vessel position signal and the vessel width signal extracts pixels that have specific positive values in both of the vessel position signal and the vessel width signal. The pixel having a specific positive value in one of the vessel position signal and the vessel width signal is expressed as the pixel having zero pixel value. Thus, the blood vessels in the vessel image signal are located in a position that is indicated (represented) by the vessel position signal and has the widths indicated (represented) by the vessel width signal. Furthermore, the vessel image signal has little noise other than the blood vessels. The vessel image signal corresponds to an image signal generated by accurately extracting only the blood vessels from the original image signal and the position and the widths of the blood vessels are extracted accurately.

Note that the reason for the vessel width signal generator 77 to use at least the B image signal, which corresponds to the blue wavelength range, of the RGB image signals to generate the vessel width signal is the same as that for the vessel position signal generator 76. The vessel width signal generator 77 may use the G image signal depending on a setting.

The vessel-enhanced image signal generator 79 generates a vessel-enhanced image signal from the original image signal that is received by the special image processor unit 67 from the image processing selector 61 and the vessel image signal generated by the vessel image signal generator 78. To be more specific, the vessel-enhanced image signal generator 79 performs the color conversion process, the color enhancement process, and the structure enhancement process on the original image signal that is received by the special image processor unit 67 from the image processing selector 61. Thereby the vessel-enhanced image signal generator 79 produces an image signal (hereinafter referred to as the base image signal), from which the vessel-enhanced image signal is produced. The base image signal corresponds to the normal image signal generated by the normal image processor unit 66. Then the vessel-enhanced image signal generator 79 superimposes the vessel image signal onto the base image signal to generate the vessel-enhanced image signal. Thereby the position and the widths of the blood vessels included in the object are enhanced accurately with little error in the vessel-enhanced image signal.

The normal image signal, which is generated by the normal image processor unit 66, and the vessel-enhanced image signal, which is generated by the special image processor unit 67, are inputted to the video signal generator 68. The video signal generator 68 converts the normal image signal and the vessel-enhanced image signal into video signals to be displayed as images on the monitor 18. The monitor 18 displays the normal image and/or the vessel-enhanced image based on the video signal(s).

Figure 10:
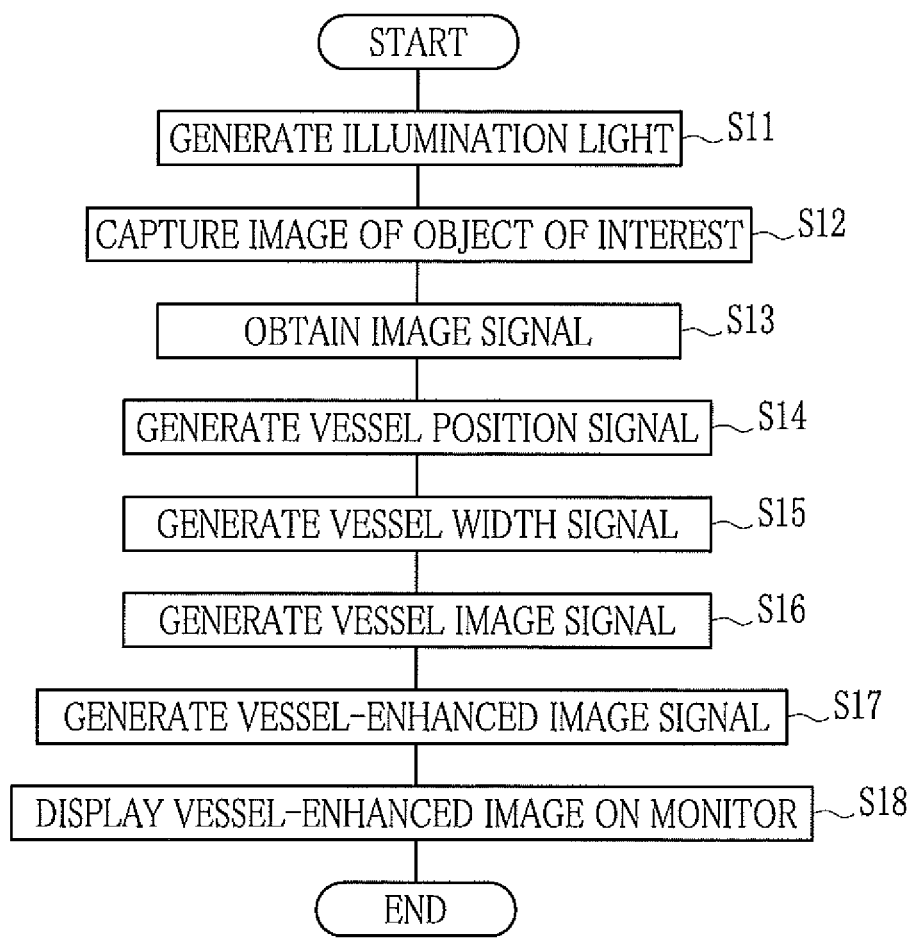
FIG. 10 is a flowchart according to a first embodiment.

Hereinafter referring to FIG. 10, steps of the image processing in the special mode are described. First, the light source unit 20 generates the illumination light (S11: an illumination generating step). The image sensor 48 captures an image of the object irradiated with the illumination light (S12: an imaging step). Then the image signal obtaining section 53 of the processor device 16 obtains image signals from the image sensor 48 (S13: an image signal obtaining step). The image signals obtained by the image signal obtaining section 53 are subjected to various processes such as the demosaicing process and the noise removal process performed by the DSP 56 and the noise remover 58, and then transmitted to the special image processor unit 67 through the image processing selector 61.

Figure 11:
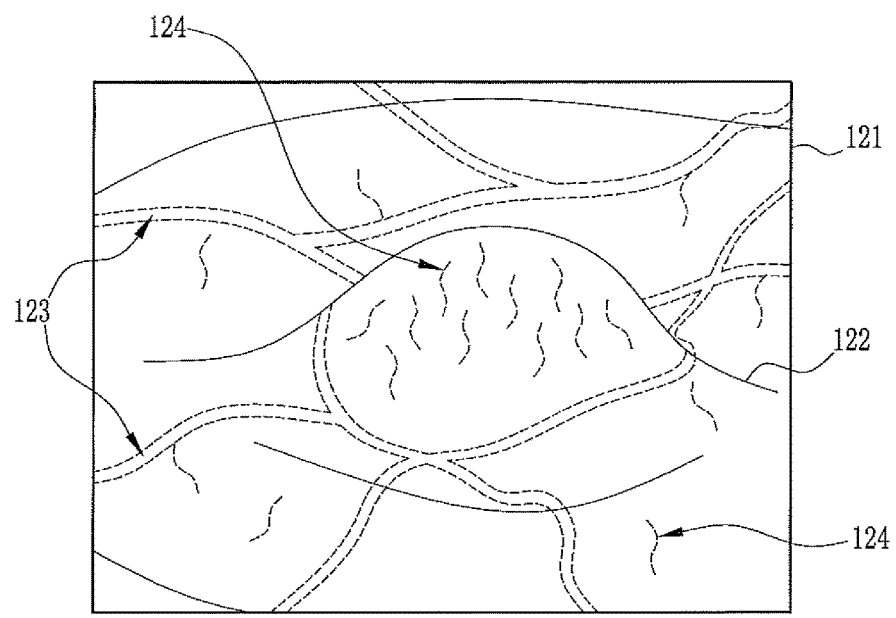
FIG. 11 is a schematic view illustrating an image generated from RGB image signals.

The special image processor unit 67 receives the RGB image signals. A color image (an image 121 illustrated in FIG. 11) produced from the RGB image signals shows a form 122, for example, the protrusion of the object, surface blood vessels 123 located in proximity to the surface layer of mucosa, and a part of the surface blood vessels 123 (hereinafter referred to as the superficial blood vessels 124) that are distributed at the depth in close proximity to the mucosal surface. The surface blood vessels 123 and the superficial blood vessels 124 are rendered observable in the image 121 because the illumination light that contains the violet light V is used.

Figure 12:
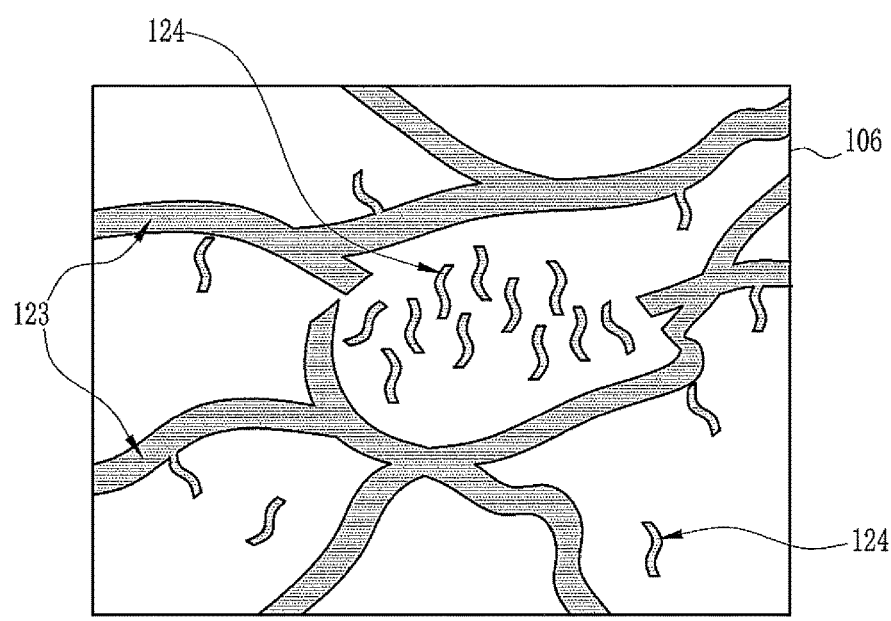
FIG. 12 is a schematic view illustrating the vessel position signal.

Upon receiving the image signals generated by capturing the image of the object, the vessel position signal generator 76 of the special image processor unit 67 performs the black top-hat transform on the received original image signal, and then binarizes the image signal with the use of a specific threshold value to generate the vessel position signal (S14: the vessel position signal generating step). As illustrated in FIG. 12, the vessel position signal 106 corresponds to an image signal that is generated by extracting the surface blood vessels 123 and the superficial blood vessels 124 from the image 121 (see FIG. 11) that is produced from the original image signal. In the vessel position signal 106, the positions of the surface blood vessels 123 and the superficial blood vessels 124 are correct but the widths (thickness or size) of the surface and superficial blood vessels 123 and 124 include errors. For example, the surface blood vessels 123 and the superficial blood vessels 124 in the vessel position signal 106 (see FIG. 12) are thicker than those in the original image signal (the image 121 shown in FIG. 11).

Figure 13:
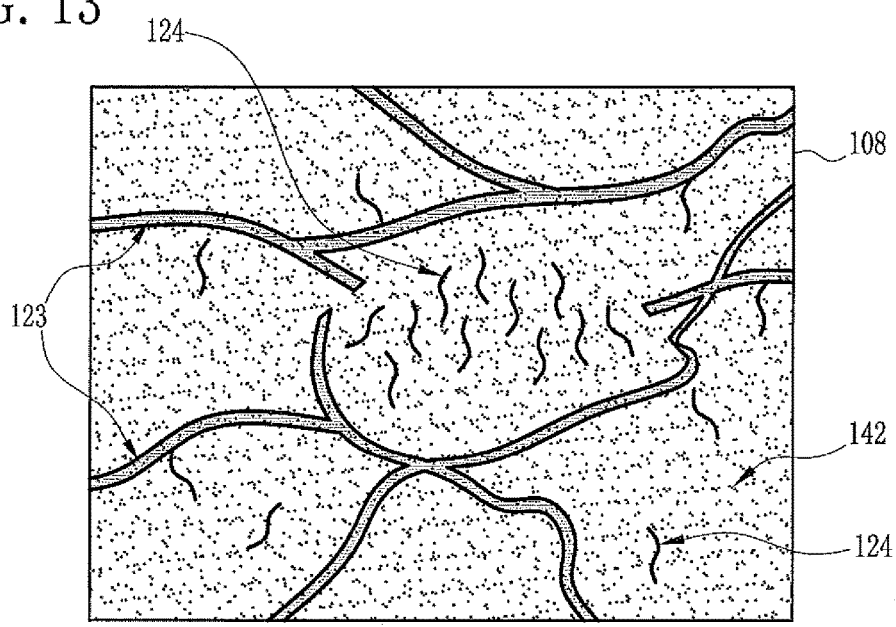
FIG. 13 is a schematic view illustrating the vessel width signal.

Upon receiving the image signal generated by capturing an image of the object, the vessel width signal generator 77 of the special image processor unit 67 performs the black top-hat transform on the received original image signal and then performs LoG filtering on the image signal that has been subjected to the black top-hat transform. The pixel values of the pixels in a region located between the zero-crossing points of the image signal that has been subjected to the LoG filtering and in which the pixels have negative pixel values are changed to specific positive values and the pixel values of the pixels outside the above-described region are changed to zero. Thereby the special image processor unit 67 generates the vessel width signal (S15: the vessel width signal generating step). As illustrated in FIG. 13, the vessel width signal 108 corresponds to an image signal generated by extracting the surface blood vessels 123 and the superficial blood vessels 124 from the image 121 (see FIG. 11) produced from the original image signal. The widths of the surface and superficial blood vessels 123 and 124 are correct in the vessel width signal 108 but the vessel width signal 108 includes noise because the LoG filter, which includes the differentiation, is used. For example, noise 142 that is not included in the original image signal (the image 121 shown in FIG. 11) or the vessel position signal 106 (see FIG. 12) appears in the vessel width signal 108 shown in FIG. 13.

Figure 14:
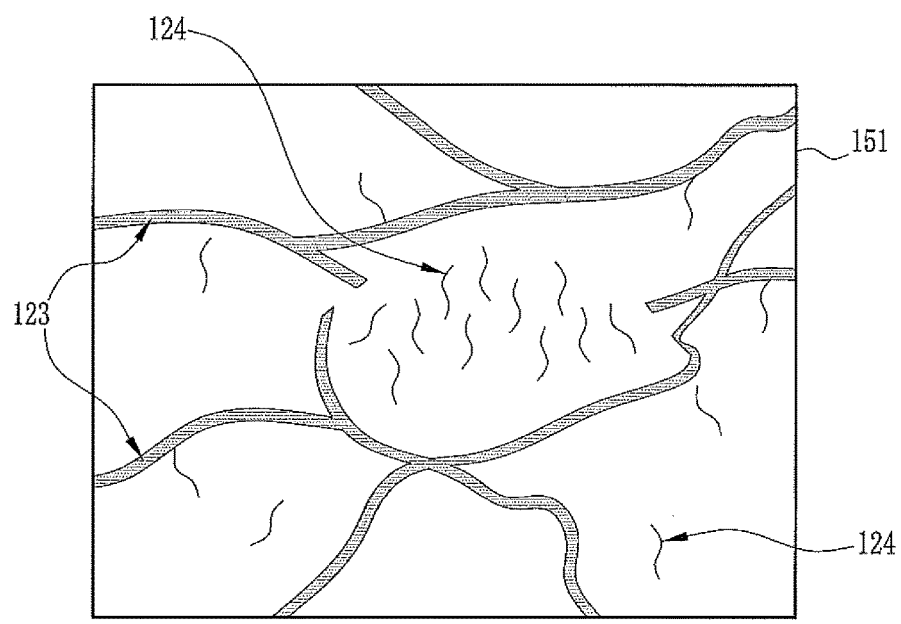
FIG. 14 is a schematic view illustrating a vessel image signal.

The special image processor unit 67 calculates the "AND" of the vessel position signal 106 and the vessel width signal 108, thereby generating the vessel image signal (S16: the vessel image signal generating step). As illustrated in FIG. 14, a vessel image signal 151 does not include the noise 142 that appears in the vessel width signal 108. The vessel image signal 151 accurately indicates (represents) the positions and the widths of the surface blood vessels 123 and the superficial blood vessels 124.

Figure 15:
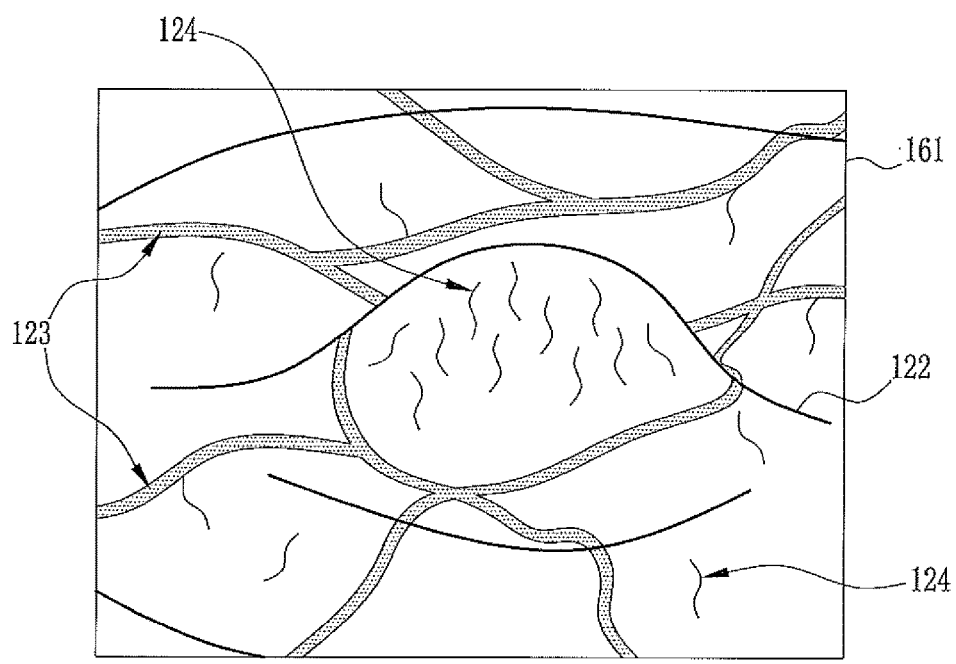
FIG. 15 is a schematic view illustrating a vessel-enhanced image signal.

The vessel image signal generator 78 of the special image processor unit 67 generates the vessel image signal 151 as described above. Then the vessel-enhanced image signal generator 79 of the special image processor unit 67 generates the color base image signal from the original image signal, and superimposes the vessel image signal 151 onto the base image signal to generate the vessel-enhanced image signal (S17: the vessel-enhanced image signal generating step). As illustrated in FIG. 15, the vessel-enhanced image signal 161 shows the form 122 such as the protrusion of the object that appear in the image 121 corresponding to the original image signal. The surface and superficial blood vessels 123 and 124 are enhanced in the vessel-enhanced image signal 161 as compared with those in the image 121 corresponding to the original image signal. The positions and the widths of the enhanced surface and superficial blood vessels 123 and 124 are correct in the vessel-enhanced image signal 161. The vessel-enhanced image signal 161 generated by the vessel-enhanced image signal generator 79 is converted by the video signal generator 68 into a video signal in a format conforming to the monitor 18 and outputted to the monitor 18 (S18).

To extract the blood vessels from the image signal generated by capturing an image of the object, the endoscope system 10 generates the vessel position signal 106, which has low noise and in which the position of the blood vessels is correct, and the vessel width signal 108, which has noise and in which the widths of the blood vessels are correct, and calculates the "AND" of the vessel position signal 106 and vessel width signal 108 as described above. Thereby the vessel image signal 151, which corresponds to an image signal generated by extracting the blood vessels from the original image signal, is generated. Thereby the endoscope system 10 accurately extracts the blood vessels and the position and the widths of the extracted blood vessels are correct. With the use of the vessel image signal 151 thus generated, the endoscope system 10 enhances and displays the blood vessels (the surface blood vessel 123, the superficial blood vessels 124, and the like) in their correct position and with their correct widths, as compared with those enhanced and displayed by a conventional endoscope system.

For example, in a case where the vessel position signal 106 is superimposed on the base image signal to enhance the blood vessels, the positions of the enhanced surface and superficial blood vessels 123 and 124 are correct but the widths thereof are incorrect. The enhanced blood vessels 123 and 124 have the widths larger than those of the blood vessels in the image 121, which corresponds to the original image signal. In a case where the vessel width signal 108 is superimposed on the base image signal to enhance the blood vessels, the widths of the enhanced surface and superficial blood vessels 123 and 124 are correct but the noise 142 makes blood vessels appear in an area where the surface blood vessels 123 and the superficial blood vessels 124 are absent in the original image 121. This provides misleading information about the presence or the absence of the surface and superficial blood vessels 123 and 124. On the other hand, the endoscope system 10 enhances and displays the surface blood vessels 123 and the superficial blood vessels 124 in their correct positions and with their correct widths, owing to the use of the vessel image signal 151 generated as described above.

Note that, in the first embodiment, each pixel of the image signal that is obtained by the special image processor unit 67 from the image processing selector 61 has a pixel value proportionate to a light receiving amount of the corresponding pixel of the image sensor 48. The vessel position signal generator 76 and the vessel width signal generator 77 generate the vessel position signal and the vessel width signal, respectively, from the image signal having the pixel values, which are proportionate to the light receiving amounts. Instead, the vessel position signal generator 76 and the vessel width signal generator 77 may perform log conversion of the pixel values, which are proportionate to the light receiving amounts, to convert the pixel values into an image signal that is proportionate to concentration (density), and then calculate the vessel position signal and the vessel width signal. Thereby the vessel position signal and the vessel width signal are calculated stably irrespective of the luminance (illumination) levels of the illumination light.

[Second Embodiment]

There are cases where a part of the blood vessels included the object is important in diagnosing a lesion, depending on a type of a disease. The position and the widths of the blood vessels located at a specific depth (or in a specific depth range) from the mucosal surface may provide important information for the diagnosis. For example, during the progress from Barrett's esophagus to the Barrett's adenocarcinoma, there is a significant change in the density of the superficial blood vessels 124, which are in a particularly shallow location under the mucosal surface, of the blood vessels (hereinafter referred to as the surface blood vessels) located in proximity to the mucosal surface. Therefore is has been considered that the staging accuracy of the Barrett's adenocarcinoma is improved by enhancing and displaying the superficial blood vessels 124 or calculating the blood vessel density of the superficial blood vessels 124. However, the method for extracting the blood vessels implemented by the conventional endoscope system cannot distinguish and extract the blood vessels located at a specific depth under the mucosal surface. The second embodiment describes an endoscope system that distinguishes the blood vessels located at the specific depth under the mucosal surface and accurately extracts the position and the widths (thickness) of the distinguished blood vessels.

Figure 16:
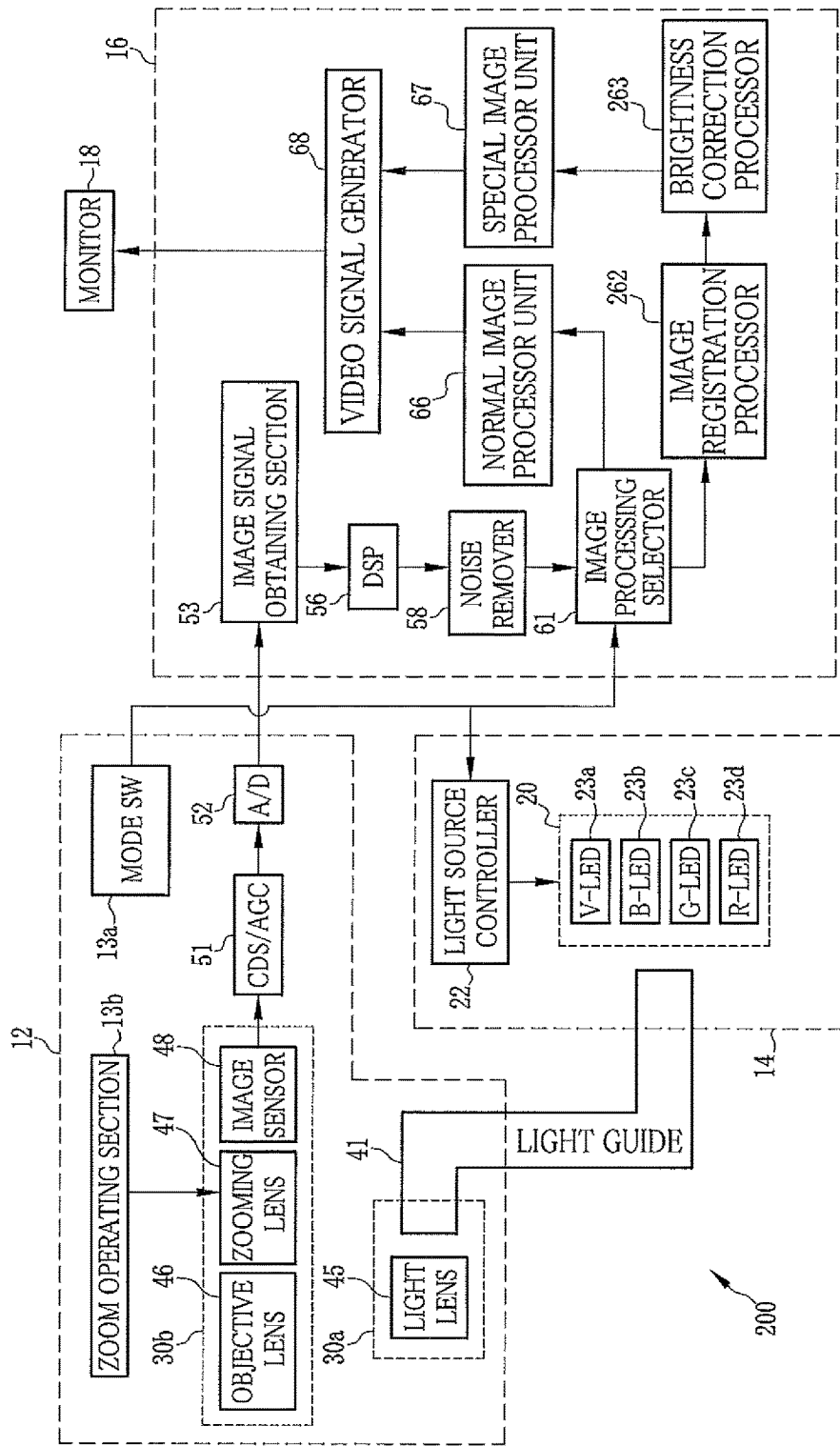
FIG. 16 is a block diagram illustrating an endoscope system according to a second embodiment.

As illustrated in FIG. 16, an endoscope system 200 according to the second embodiment comprises the processor device 16 that comprises an image registration processor 262 and a brightness correction processor 263. Other than those, the configuration of the endoscope system 200 is similar to that of the endoscope system 10 of the first embodiment. However, some parts differ in operation from those of the first embodiment.

In the normal mode in this embodiment, the light source controller 22 turns on all of the V-LED 23a, the B-LED 23b, the G-LED 23c, and the R-LED 23d, in a manner similar to the first embodiment. In the special mode in this embodiment, the light source controller 22 controls the light source unit 20 to perform a first emission mode and a second emission mode, unlike the first embodiment. In the first emission mode, the light source controller 22 turns on the V-LED 23a and turns off the B-LED 23b. In the second emission mode, the light source controller 22 turns off the V-LED 23a and turns on the B-LED 23b. In the second emission mode, the G-LED 23c and the R-LED 23d are turned on together with the B-LED 23b. Accordingly, in the first emission mode in the special mode, the violet light V is used as the illumination light. In the second emission mode in the special mode, white light composed of the blue light B, the green light G, and the red light R is used as the illumination light. The white light used in the second emission mode differs in wavelength range from the violet light V used in the first emission mode. The violet light V used in the first emission mode is the first illumination light, by way of example. The blue light B included in the white light used in the second emission mode is the second illumination light, by way of example. The first illumination light differs from the second illumination light in wavelength range or in composition of the wavelength components (the so-called optical spectrums). In other words, the second illumination light may be the illumination light that differs in wavelength range from the first illumination light or the illumination light that has substantially the same wavelength range as that of the first illumination light but differs in optical spectrum from the first illumination light.

In a case where the light source unit 20 is set to the first emission mode in the special mode of this embodiment, the violet light V is used as the illumination light. The image sensor 48 captures an image of the object irradiated with the violet light V and outputs a first blue image signal (hereinafter referred to as the B1 image signal) from the B pixels. In a case where the light source unit 20 is set to the second emission mode, the white light composed of the blue light B, the green light G, and the red light R is used as the illumination light. The image sensor 48 captures each color image of the object irradiated with the blue light B, the green light G, and the red light R and outputs a second blue image signal (hereinafter referred to as the B2 image signal) from the B pixels, a green image signal (hereinafter referred to as G image signal) from the G pixels, and a red image signal (hereinafter referred to as the R image signal) from the R pixels. The B2 image signal corresponds to the blue light B. The G image signal corresponds to the green light G. The R image signal corresponds to the red light R. The B1 image signal corresponds to a first image signal, for example. The B2 image signal corresponds to a second image signal, for example.

In the special mode of this embodiment, four image signals (the B1 image signal, the B2 image signal, the G image signal, and the R image signal) are inputted to the special image processor unit 67. The B1 image signal corresponds to the violet light V and is obtained by capturing an image of the object irradiated with the illumination light of the first emission mode. The B2 image signal corresponds to the blue light B and is obtained by capturing an image of the object irradiated with the illumination light of the second emission mode. The G image signal corresponds to the green light G of the second emission mode. The R image signal corresponds to the red light R of the second emission mode. These image signals are inputted through the image registration processor 262 and the brightness correction processor 263.

The image registration processor 262 performs image registration among the B1 image signal and the image signals (the B2 image signal, the G image signal, and the R image signal), which are obtained sequentially. The image registration processor 262 corrects at least one of the B1 image signal obtained in the first emission mode and the image signals (the B2 image signal, the G image signal, and the R image signal) obtained in the second emission mode.

The brightness correction processor 263 corrects the brightness of at least one of the B1 image signal obtained in the first emission mode and the image signals (the B2 image signal, the G image signal, and the R image signal) obtained in the second emission mode such that the brightness values of the B1 and B2 image signals that have been registered by the image registration processor 262 have a specific ratio. To be more specific, the light quantity ratio between the violet light V in the first emission mode and the blue light B in the second emission mode is known, so that the gain correction is performed using the known light quantity ratio so as to achieve the brightness values obtained by applying the violet light V and the blue light B, respectively, of the same light quantity, to the object. Thereby the brightness of the B1 image signal is the same as that of the B2 image signal.

The special image processor unit 67 comprises the vessel position signal generator 76, the vessel width signal generator 77, the vessel image signal generator 78, and the vessel-enhanced image signal generator 79 (see FIG. 5), similar to the first embodiment. However, some parts differ in operation from those of the first embodiment.

In this embodiment, the vessel position signal generator 76 performs the log conversion on each of the B1 image signal, which corresponds to the violet light V, and the B2 image signal, which corresponds to the blue light B, and generates a differential image signal through calculating a differential (difference) between the B2 and B1 image signals that have been subjected to the log conversion. The vessel position signal generator 76 performs the white top-hat transform on the calculated differential image signal to extract blood vessels located at a specific depth in the object from the inputted image signal. In this embodiment, after the log conversion, the B1 image signal is subtracted from the B2 image signal to generate the differential image signal. The vessel position signal generator 76 binarizes the differential image signal that has been subjected to the white top-hat transform, to generate the vessel position signal, in which the pixel value of the pixels representing blood vessels at a specific depth has a specific positive value (for example, "1") and the pixel value of the remaining pixels is "zero".

Figure 17:
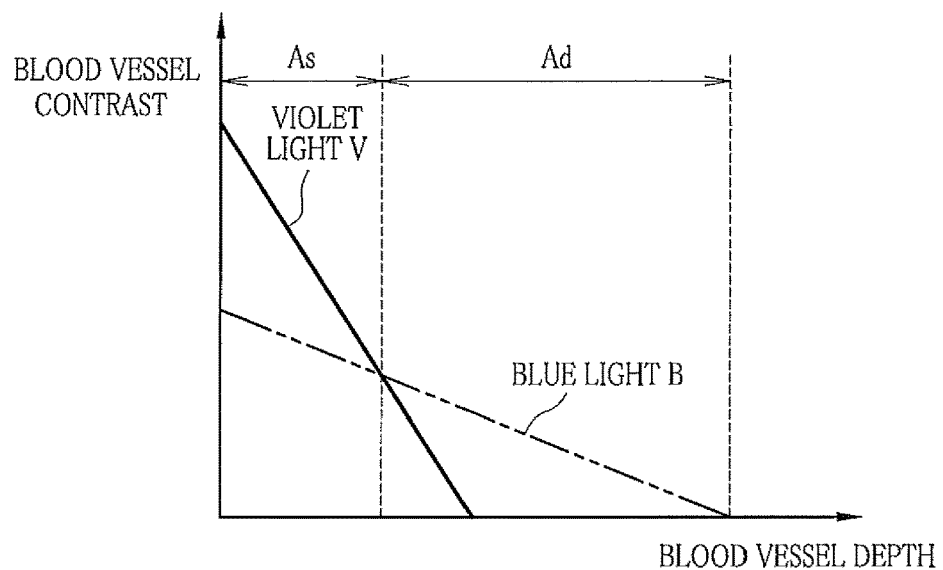
FIG. 17 is a graph schematically illustrating a relationship between blood vessel depth and blood vessel contrast for each wavelength of illumination light.

As illustrated in FIG. 17, the violet light V has the wavelengths shorter than those of the blue light B, so that the penetration depth into the object is small. Accordingly, the violet light V allows imaging the blood vessels in a shallow position "As" under the mucosal surface relative to the blood vessels imaged using the blue light B. However, the blood vessel contrast (the ratio between the amount of light reflected from the blood vessels and the amount of light reflected from the surrounding mucosa) of the blood vessels located in the shallow position As is higher than that obtained by using the blue light B. The blue light B has the wavelengths longer than those of the violet light V, so that the penetration depth into the object is large. Accordingly, the blue light B allows imaging the blood vessels located in a deep position "Ad" under the mucosal surface relative to the blood vessels imaged using the violet light V. However, the contrast of the blood vessels in the shallow position As is lower than that obtained by using the violet light V. In a case where the B1 image signal, which corresponds to the violet light V, is subtracted from the B2 image signal, which corresponds to the blue light B, the pixel representing the superficial blood vessels located in the shallow portion As under the mucosal surface has a high pixel value (white color) and the pixel representing the surface blood vessels located in the deep position Ad, which is deeper than the position of the superficial blood vessels, has a low pixel value (black color).

The white top-hat transform is an morphological operation and is a process for subtracting an image signal that has been subjected to an opening operation from the original image signal. The opening operation is a process to perform the dilation, which expands the bright region, after the erosion, which reduces the bright region. In other words, the white top-hat transform is a process to extract the pixels with high pixel values (the bright pixels) as compared with the adjacent pixels while the noise is removed. In a case where the white top-hat transform is performed on the differential image signal, which is generated by subtracting the B1 image signal corresponding to the violet light V from the B2 image signal corresponding to the blue light B, the superficial blood vessels with high pixels values are distinguished from the surface blood vessels located in the relatively deep position Ad and extracted.

Figure 18:
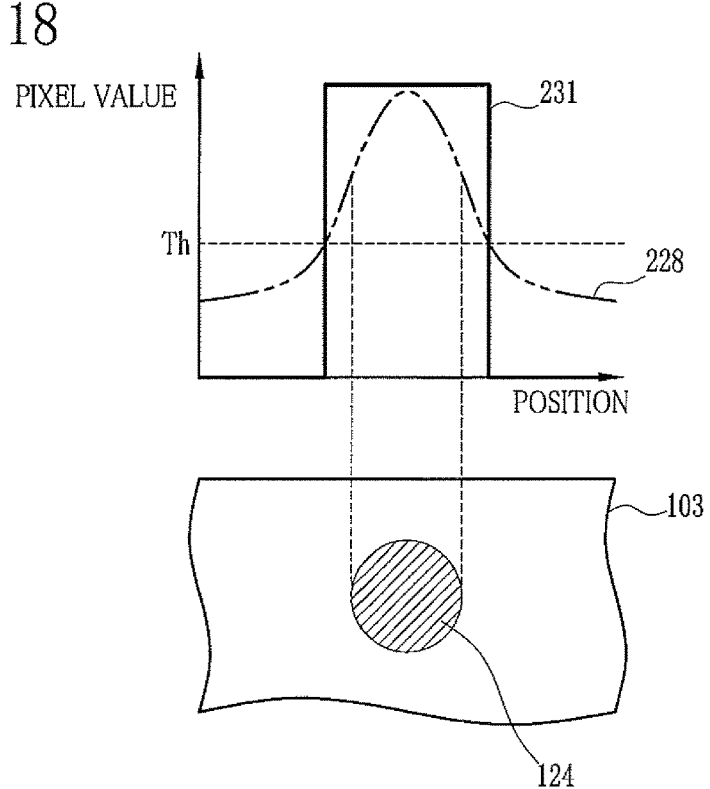
FIG. 18 is an explanatory view illustrating a method for generating the vessel position signal.

In the case where the size, shape, and the like of the structuring element (kernel) to be used for the white top-hat transform is set properly, substantially only the superficial blood vessels are accurately extracted by binarizing the image signal that has been subjected to the white top-hat transform. For this reason, the vessel position signal generated by the vessel position signal generator 76 accurately indicates (represents) the position of the superficial blood vessels. However, the widths (the thickness or the size in the image) of the superficial blood vessels represented by the vessel position signal are incorrect and include errors. This is because the light reflected from the superficial blood vessels is diffused by scattering or the like while the light is transmitted through the object 103, as in the case of the light 102 reflected from the blood vessel 101 described in the first embodiment (see FIG. 6). In the case where the distribution of the amount of light received by the image sensor 48 spreads out into a concave Gaussian function shape due to the diffusion (scattering) of the light reflected from the superficial blood vessels, as in the case of the light 102 reflected from the blood vessel 101, a differential image signal 228 obtained after the white top-hat transform takes a convex Gaussian function shape (see FIG. 18). The differential image signal 228 obtained after the white top-hat transform is binarized to generate a vessel position signal 231. In this case, the width of the superficial blood vessel 124 in the vessel position signal 231 varies depending on the setting of a threshold value Th for the binarization. Thus, the vessel position signal 231 indicates (represents) the correct position of the superficial blood vessel 124 but the width of the superficial blood vessel 124 includes an error. Note that "the position of the superficial blood vessel 124 is correct" means that there is low noise and substantially only the superficial blood vessel 124 is extracted.

Of the B1 image signal and the B2 image signal, the vessel width signal generator 77 performs LoG filtering on the B1 image signal, in which the contrast of the superficial blood vessels is high, in this embodiment. The binary vessel width signal is generated by using the zero-crossing point of the image signal that has been subjected to the LoG filtering.

Figure 19:
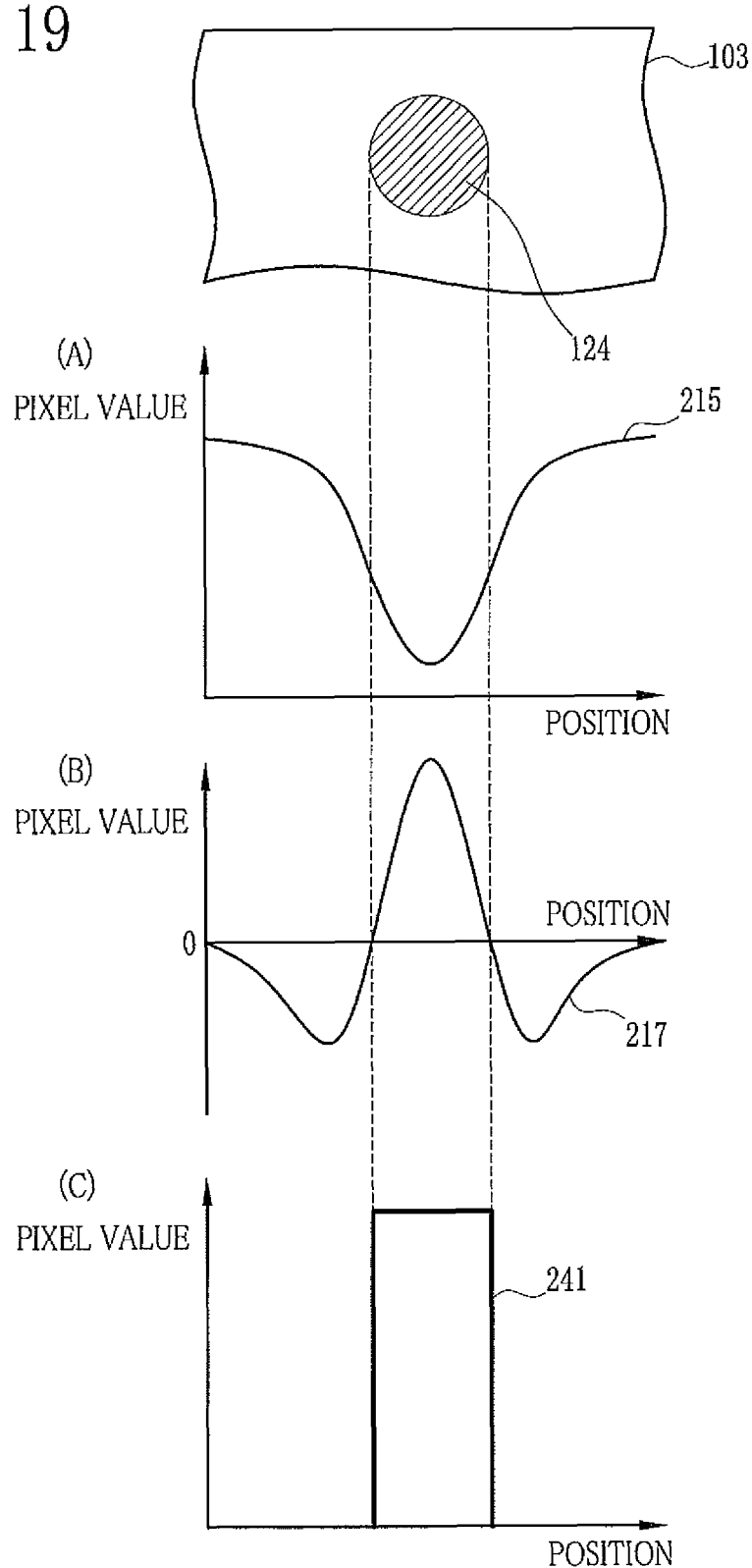
FIG. 19 is an explanatory view illustrating a method for generating the vessel width signal.

For example, in the case where LoG filtering is performed on a B1 image signal 215 shown in a part (A) of FIG. 19, a zero-crossing point of an image signal 217 obtained after the LoG filtering substantially accurately indicates an edge of the superficial blood vessel 124. For this reason, as shown in a part (C) of FIG. 19, the vessel width signal generator 77 extracts a region between the zero-crossing points and in which the pixel values take positive values, from the B1 image signal 217 obtained after the LoG filtering. Thereby the vessel width signal generator 77 generates the vessel width signal 241. In the vessel width signal 241, a region corresponding to the blood vessels is represented by "white" pixels having the specific positive value (for example, "1"), whereas a region other than the blood vessels is represented by "black" pixels having the pixel value "zero". As is obvious from the above-described method for generating the vessel width signal 241, the width of the superficial blood vessel 124 is correct in the vessel width signal 241. However, since the Laplacian filter, which performs the differentiation, is used, an extremely small signal is detected. Therefore the vessel width signal 241 accurately indicates the width of the superficial blood vessel 124 but includes the noise (that is, the positional error of the superficial blood vessel 124) other than the superficial blood vessel 124.

The vessel image signal generator 78 calculates the "AND" of the vessel position signal and the vessel width signal to generate the vessel image signal, in a manner similar to the first embodiment. In this embodiment, however, the vessel position signal is generated by performing the white top-hat transform on the differential image signal, which is obtained by subtracting the B1 image signal from the B2 image signal, and then binarizing the result thereof, as described above. The vessel width signal is generated by performing the LOG filtering on the B1 image signal, in which the contrast of the superficial blood vessels is high, of the B1 and B2 image signals, and then binarizing the result thereof, as described above. Therefore the vessel image signal generated by the vessel image signal generator 78 corresponds to an image signal generated by extracting the superficial blood vessels in their correct position and with their correct widths from the original image signal.

In this embodiment, the vessel-enhanced image signal generator 79 generates the vessel-enhanced image signal from or based on the B2 image signal, the G image signal, the R image signal, and the vessel image signal that is generated by the vessel image signal generator 78. To be more specific, first, the vessel-enhanced image signal generator 79 performs the color conversion process, the color enhancement process, and the structure enhancement process on the B2 image signal, the G image signal, and the R image signal to generate the base image signal. Then, the vessel-enhanced image signal generator 79 superimposes the vessel image signal onto the base image signal to generate the vessel-enhanced image signal. Thereby the position and the widths of the superficial blood vessels 124 in the object are enhanced correctly with little error in the vessel-enhanced image signal of this embodiment.

Figure 20:
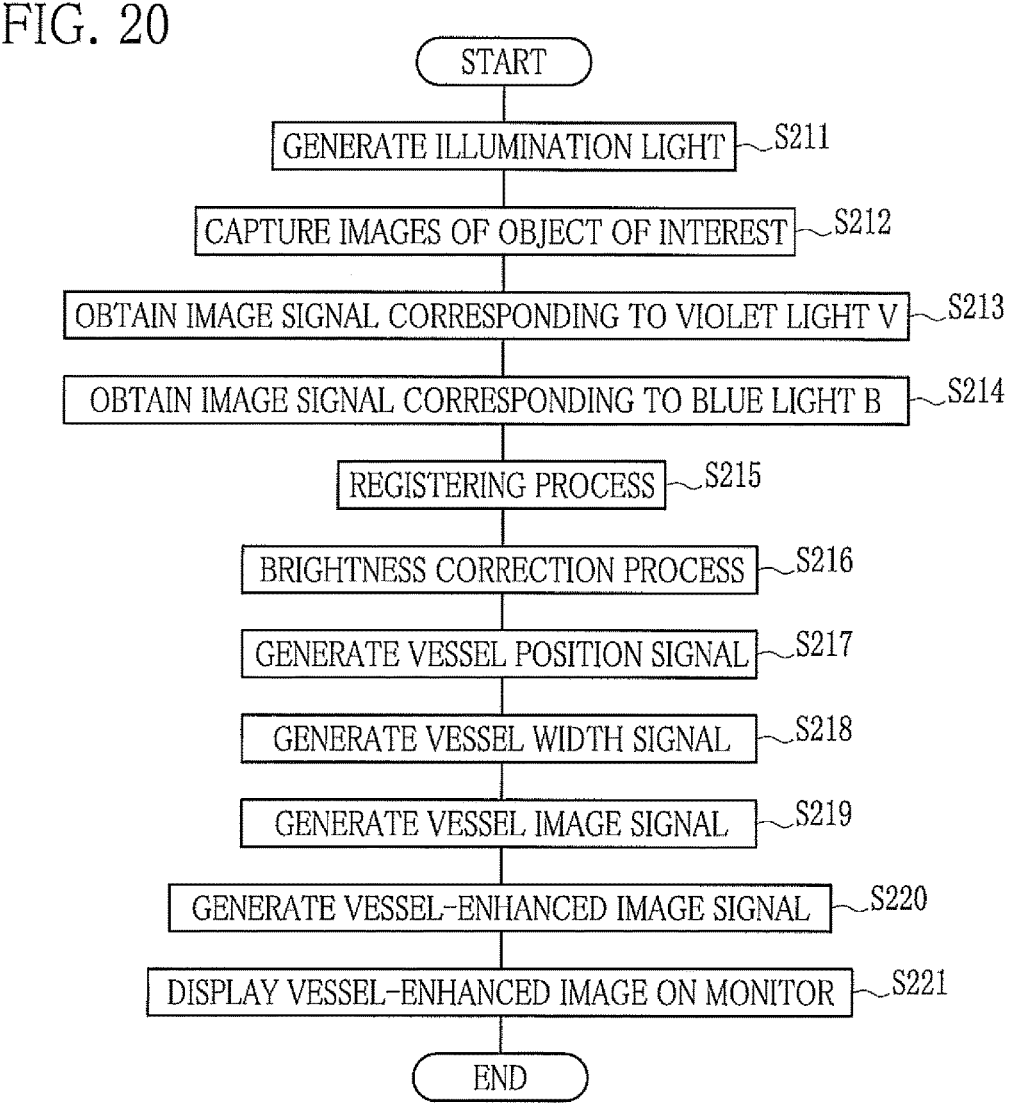
FIG. 20 is a flowchart according to a second embodiment.

Hereinafter, referring to FIG. 20, steps of image processing in the special mode of this embodiment are described. First, the light source unit 20 generates the illumination light in each of the first emission mode and the second emission mode. The light source unit 20 generates the violet light V as the illumination light and the white light composed of the blue light B, the green light G, and the red light R as the illumination light (S211: illumination generating step). To be more specific, the light source unit 20 emits the violet light V in the first emission mode and emits the white light composed of the blue light B, the green light G, and the red light R in the second emission mode. The image sensor 48 captures an image of the object of interest irradiated with each illumination light (S212: imaging step). The image signal obtaining section 53 of the processor device 16 obtains the image signals obtained by capturing an image of the object irradiated with the illumination light. To be more specific, the image signal obtaining section 53 obtains the B1 image signal corresponding to the violet light V (S213: first image signal obtaining step). The image signal obtaining section 53 also obtains the B2 image signal corresponding to the blue light B, the G image signal corresponding to the green light G, and the R image signal corresponding to the red light F. (S214: second image signal obtaining step). The image signals sequentially obtained by the image signal obtaining section 53 are subjected to the image registration performed by the image registration processor 262 (S215: image registration step) and subjected to the brightness correction performed by the brightness correction processor 263 (S216: brightness correction step), and then inputted to the special image processor unit 67.

The color image 121 (see FIG. 11) generated by the special image processor unit 67 from or based on the B2 image signal, the G image signal, and the R image signal renders the form 122 such as the protrusion on the object, the surface blood vessels 123, and the superficial blood vessel 124 observable.

Figure 21:
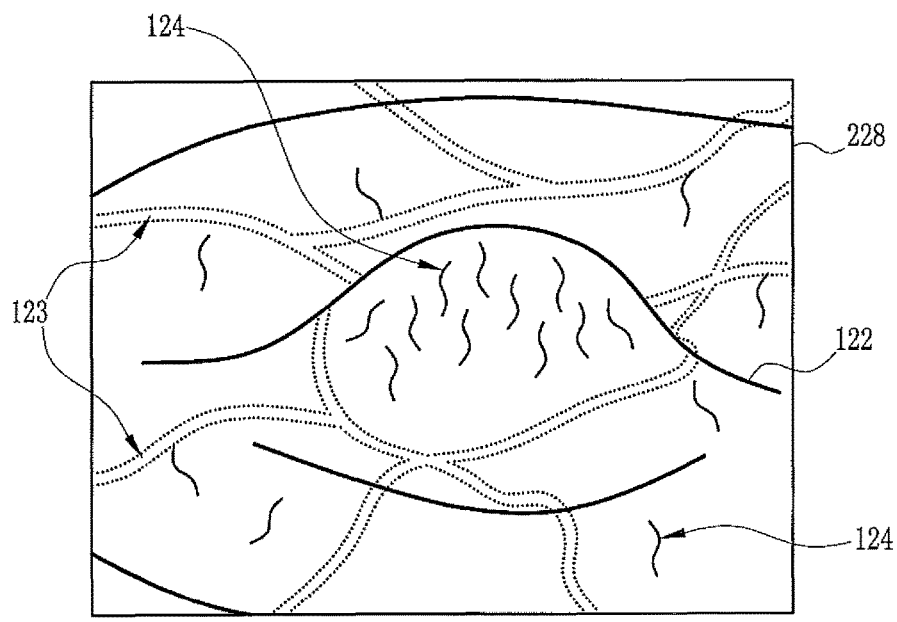
FIG. 21 is a schematic view illustrating a differential image signal.
Figure 22:
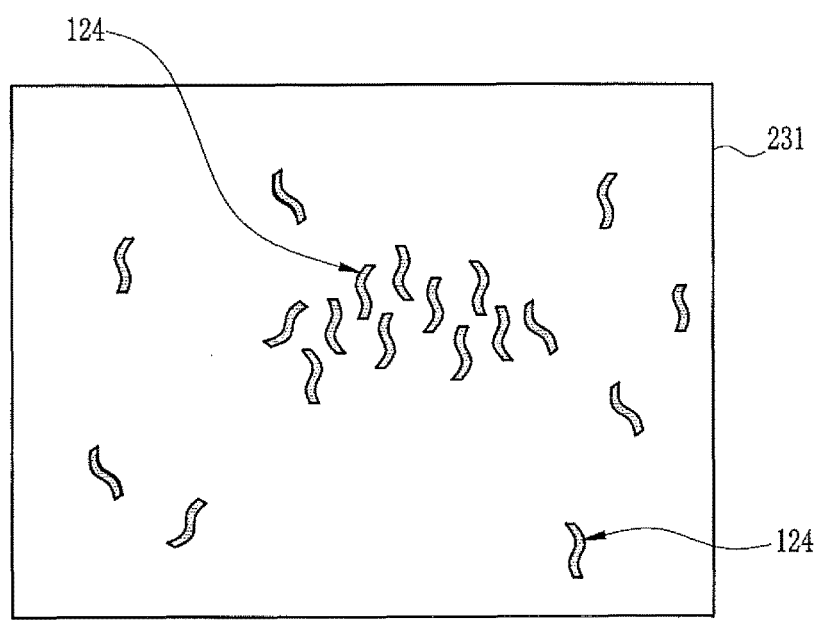
FIG. 22 is a schematic view illustrating the vessel position signal.

Upon receiving each image signal, which is obtained by imaging the object, the vessel position signal generator 76 of the special image processor unit 67 subtracts the B1 image signal, which corresponds to the violet light V, from the B2 image signal, which corresponds to the blue light B, to generate the differential image signal. In the differential image signal 228, the pixel value corresponding to the surface blood vessels 123, which are located in the relatively deep position, is low and the pixel value corresponding to the superficial blood vessel 124 is high, relative to those in the original image signal (for example, the image 121 shown in FIG. 11). As illustrated in FIG. 21, the difference between the superficial blood vessels 124 and the surface blood vessels, which are located in the relatively deep position, is more apparent in the differential image signal 228 than that in the original image signal (for example, the image 121 shown in FIG. 12). The vessel position signal generator 76 performs the white top-hat transform on the generated differential image signal 228, and then binarizes the image signal with the use of a specific threshold value. Thereby the vessel position signal generator 76 generates the vessel position signal 231 (S217: the vessel position signal generating step). As illustrated in FIG. 22, the vessel position signal 231 corresponds to an image signal generated by extracting the superficial blood vessels 124 from the differential image signal 228. The vessel position signal 231 accurately indicates the position of the superficial blood vessels 124, but the widths (the thickness) of the superficial blood vessels 124 include errors. For example, the superficial blood vessels 124 in the vessel position signal 231 (see FIG. 22) are thicker than those in the differential image signal 228 (see FIG. 21).

Figure 23:
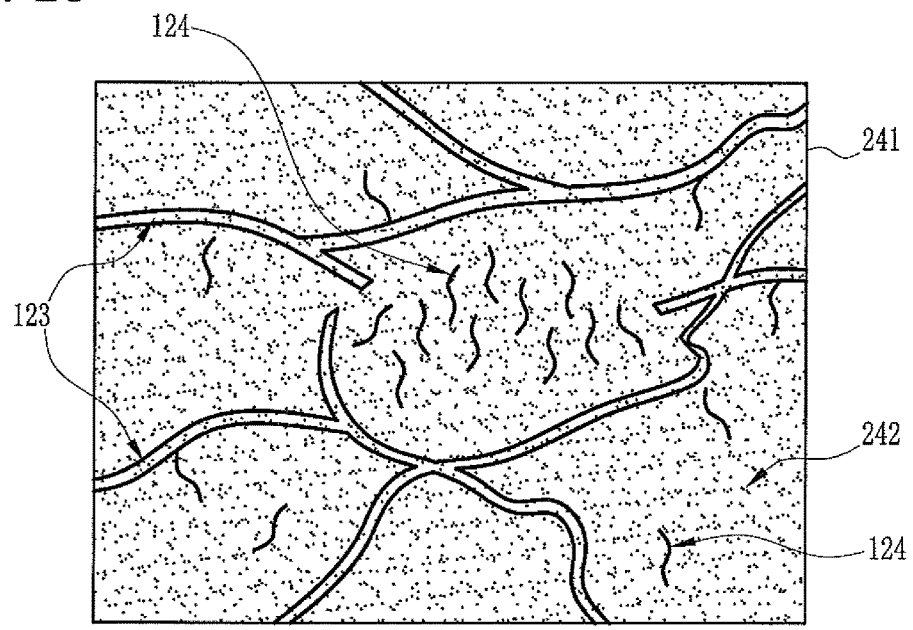
FIG. 23 is a schematic view illustrating the vessel width signal.

Upon the special image processor unit 67 receives the image signal that is generated by imaging the object, the vessel width signal generator 77 performs LoG filtering on the B1 image signal, in which the contrast of the superficial blood vessels is high. The pixel value of the pixels in a region located between the zero-crossing points of the image signal that has been subjected to the LoG filtering and in which the pixel values take positive values is set to a specific positive value and the pixel value of the pixels located in the remaining regions is set to zero. Thereby the vessel width signal is generated (S218: the vessel width signal generating step). As illustrated in FIG. 23, the widths (the thicknesses) of the superficial blood vessels 124 are correct in the vessel width signal 241. However, the vessel width signal 241 includes the surface blood vessels 123, which are located in the relatively deep position. The vessel width signal 241 also includes noise 242 because the LoG filter, which performs the differentiation, is used.

Figure 24:
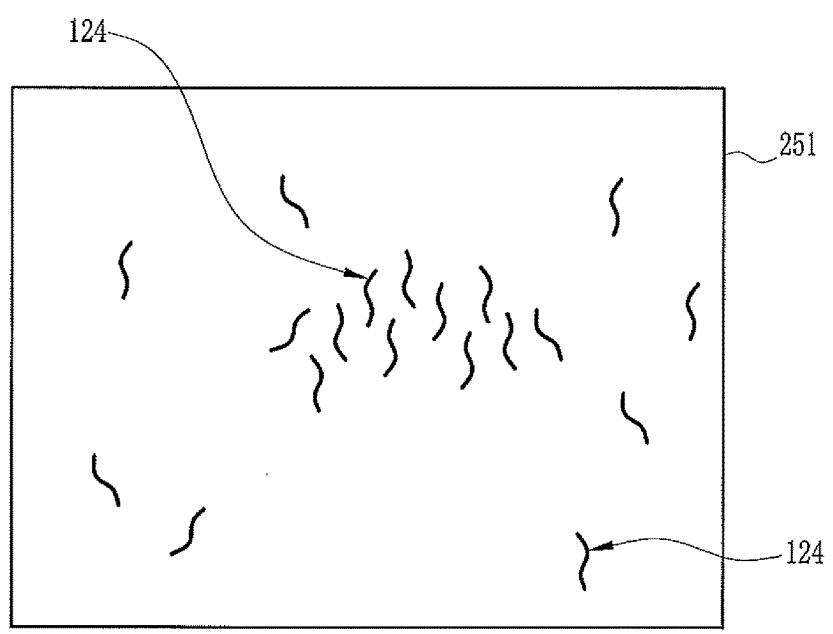
FIG. 24 is a schematic view illustrating the vessel image signal.

The special image processor unit 67 calculates an "AND" of the vessel position signal 231 and the vessel width signal 241, thereby generating a vessel image signal 251 (S219: the vessel image signal generating step). As illustrated in FIG. 24, the vessel image signal 251 eliminates the noise 242, which appears in the vessel width signal 241. The position and the widths (the thicknesses) of the superficial blood vessel 124 are correct in the vessel image signal 251.

Figure 25:
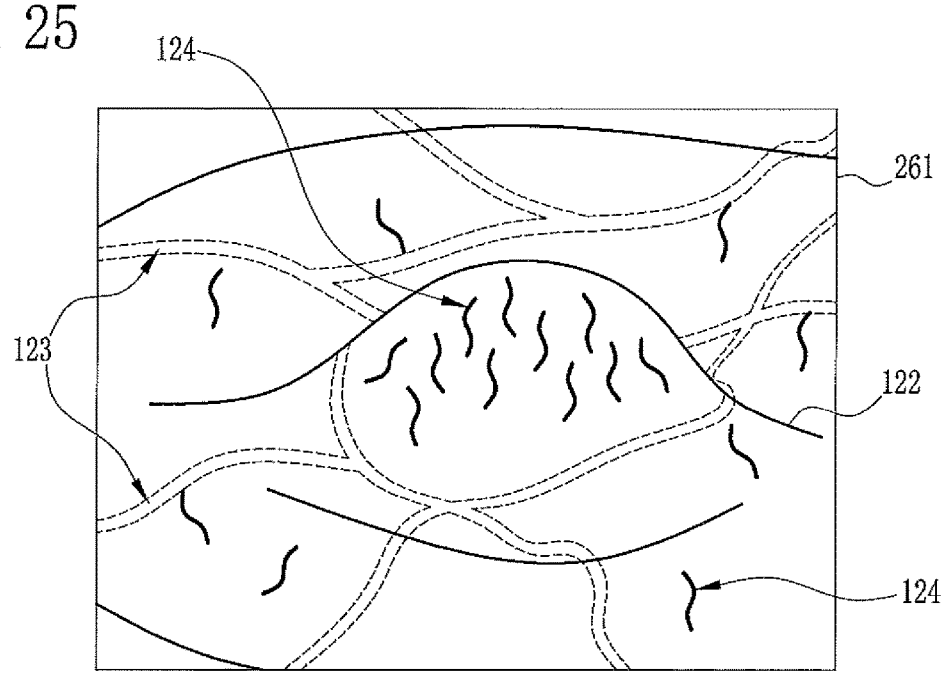
FIG. 25 is a schematic view illustrating the vessel-enhanced image signal.

The vessel image signal generator 78 of the special image processor unit 67 generates the vessel image signal 151 as described above. The vessel-enhanced image signal generator 79 of the special image processor unit 67 generates the color base image signal from the B2 image signal, the G image signal, and the R image signal and superimposes the vessel image signal 251 onto the generated base image signal (S220: the vessel-enhanced image signal generating step). As illustrated in FIG. 25, the vessel-enhanced image signal 261 renders the form 122 such as a protrusion on the object observable and enhances the superficial blood vessels 124. The position and the widths of the superficial blood vessels 124 are correct in the vessel-enhanced image signal 261. The video signal generator 68 converts the vessel-enhanced image signal 261, which is generated by the vessel-enhanced image signal generator 79, into a signal in the format conforming to the monitor 18, and the converted signal is outputted and displayed on the monitor 18 (S221).

As described above, in order to extract the blood vessels from the image signals generated by imaging the object, the endoscope system 200 of the second embodiment calculates a differential image signal, which is generated by subtracting the B1 image signal (the first image signal) from the B2 image signal (the second image signal). The B1 image signal (the first image signal) is generated by imaging the object irradiated with the violet light (the first illumination light). The B2 image signal (the second image signal) is generated by imaging the object irradiated with the blue light B (the second illumination light), which differs from the violet light V in wavelength range, the green light G, and the red light R, and corresponds to the blue light B. The vessel position signal 231, which has low noise and in which the position of the blood vessels is correct, is generated from the differential image signal. Of the B1 image signal and the B2 image signal, the B1 image signal, in which the contrast of the superficial blood vessels 124 is high, is used to generate the vessel width signal 241, in which the noise is included but the widths of the blood vessels are correct. The vessel image signal 251, which represents the superficial blood vessels 124 extracted from original image signal, is generated by calculating the "AND" of the vessel position signal 231 and the vessel width signal 241. Thereby the endoscope system 200 of the second embodiment accurately extracts both the position and the widths of the superficial blood vessels 124, distinguished from the surface blood vessels 123, for example. Owing to the use of the vessel image signal 251, the endoscope system 200 of the second embodiment accurately enhances and displays the superficial blood vessels 124 in their correct position and with their correct widths, as compared with the case of the conventional endoscope system for enhancing and displaying the blood vessels.

For example, in the case where the blood vessels are enhanced by superimposing the vessel position signal 231 onto the base image signal, the position of the enhanced superficial blood vessels 124 is correct but the widths thereof are incorrect. In other words, the enhanced superficial blood vessels 124 are thicker than the superficial blood vessels displayed in the image 121, which corresponds to the original image signal. In the case where the blood vessels are enhanced by superimposing the vessel width signal 241 onto the base image signal, the thicknesses of the enhanced superficial blood vessels 124 are correct but the noise 242 and the surface blood vessel 123, which are located in the relatively deep position, are also included. This may provide misleading information about the presence or the absence and the density of the superficial blood vessels 124. The endoscope system 200 of the second embodiment, on the other hand, uses the vessel image signal 251 generated as described above. Thereby the position and the widths of the superficial blood vessels 124 are enhanced and displayed correctly.

In the second embodiment, the vessel position signal generator 76 subtracts the B1 image signal corresponding to the violet light V from the B2 image signal corresponding to the blue light B to generate the differential image signal 228. Thereby the vessel position signal generator 76 extracts the superficial blood vessels 124 located in the especially shallow position "As" below the mucosal surface, from the blood vessels that are rendered observable by the violet light V and the blue light B. Note that, in the case where the differential image signal is generated by subtracting the B2 image signal from the B1 image signal, the superficial blood vessels 124 are eliminated from the surface blood vessels and only the surface blood vessels 123 located in the relatively deep position are extracted. In this case, the vessel width signal generator 77 uses the B2 image signal, in which the contrast of the surface blood vessels 123 located in the relatively deep position is high.

In the second embodiment, the B1 image signal corresponding to the violet light V and the B2 image signal corresponding to the blue light B are used. Note that, for example, first illumination light in a first green wavelength range and second illumination light in a second green wavelength range may be used for imaging the object, thereby generating a first green image signal and a second green image signal, respectively. The second green wavelength range differs from the first illumination light in wavelength range or optical spectrum. With the use of the first and second green image signals, the blood vessels located in a position shallower or deeper than a specific depth are accurately extracted from the blood vessels rendered observable by the green light, in a manner similar to the first embodiment. The position and the widths of the extracted blood vessels are correct. Any combination of the first illumination light and the second illumination light is used. However, the illumination light used for extracting the blood vessels is preferred to be narrowband light. The light source unit 20 may comprise an optical filter for generating the narrowband light. To extract the superficial blood vessels 124 as described in the second embodiment, the violet light V having the center wavelength of 405±10 nm and the blue light having the center wavelength of 445±10 nm are preferably used. The blue light having the center wavelength of 445±10 nm is generated from the blue light B with the use of an optical filter that cuts a longer wavelength component of the light from the B-LED 23b. The optical filter is placed in the light path of the light from the B-LED 23b.

Note that, in the second embodiment, each pixel of the image signal received by the special image processor unit 67 from the image processing selector 61 has a pixel value that is proportionate to the amount of light received by the corresponding pixel of the image sensor 48. The vessel position signal generator 76 performs the log conversion of the B1 and B2 image signals, which have the pixel values proportionate to the amounts of light received. The vessel position signal generator 76 generates the differential image signal from the B1 and B2 image signals that have been subjected to the log conversion. Thereby the image signals are proportionate to the concentration (density). The vessel position signal and the vessel width signal are generated stably irrespective of the luminance level by generating the differential image signal from the B1 and B2 image signals that have been subjected to the log conversion. Instead of generating the differential image signal from the B1 and B2 image signals that have been subjected to the log conversion as described in the first to third embodiments, a ratio may be calculated on a pixel-by-pixel basis. Thereby, a ratio between the B1 image signal and the B2 image signal (hereinafter simply referred to as the signal ratio) is calculated. The differential image signal may be generated by the log conversion of the signal ratio. Also in this case, the vessel position signal and the vessel width signal are generated stably irrespective of the luminance level of the illumination light, as in the case of the first to third embodiments. In the case where the luminance levels of the first illumination light and the second illumination light are constant or stable, the differential image signal may be generated using the B1 and B2 image signals obtained before the log conversion or the signal ratio may be used instead of the differential image signal.

[Third Embodiment]

In the above first and second embodiments, the vessel position signal generator 76 generates the vessel position signal from the image signal inputted to the special image processor unit 67. The vessel width signal generator 77 generates the vessel width signal from the image signal inputted to the special image processor unit 67. In other words, the vessel position signal generator 76 and the vessel width signal generator 77 generate the vessel position signal and the vessel width signal, respectively, from the image signal that is generated by imaging the object. However, the image signal generated by imaging the object may include noise that hinders the extraction of the blood vessels or may result in incorrect extraction, depending on the imaging conditions (e.g. how the object is illuminated). The noise that hinders the extraction of the blood vessels or may result in the incorrect extraction of the blood vessels is referred to as "artifact."

Figure 26:
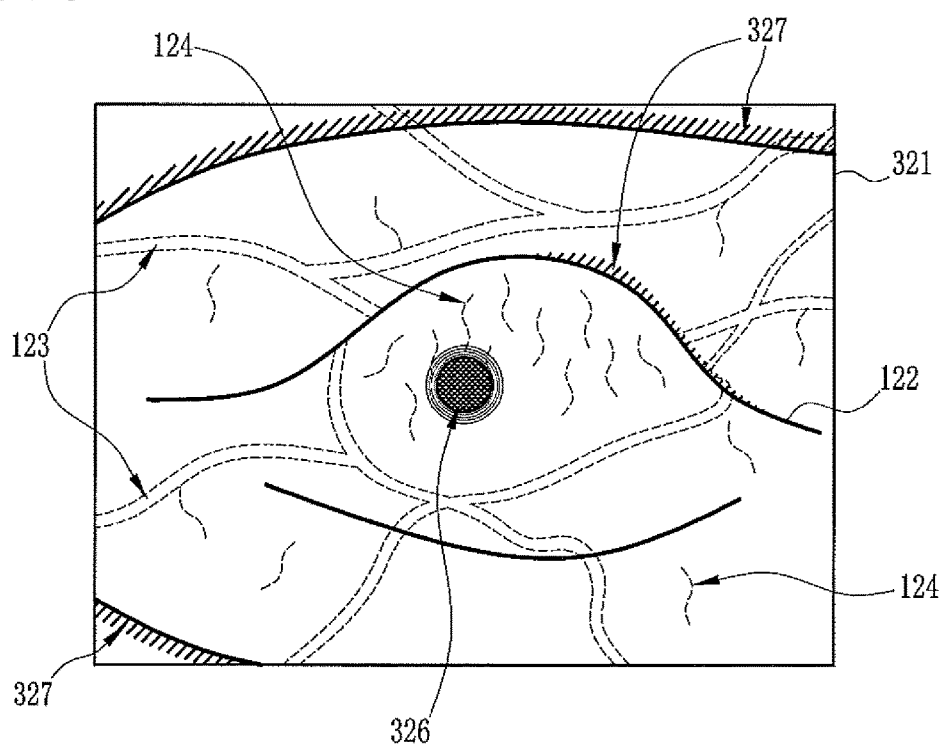
FIG. 26 is a schematic view illustrating an image with artifact.

For example, as illustrated in FIG. 26, an image signal 321, which is generated by imaging the object, may include the artifact such as halation 326 and shadows 327 that are caused by the illumination light. The halation 326 refers to an area in which the amount of the reflected illumination light is locally high due to a droplet on the object or the form 122 such as the protrusion on the object. The pixel values vary (fluctuate) significantly in the proximity of the border of the halation 326, causing the noise composed of alternating bright and dark lines. In the presence of the halation 326, the dark lines of the noise appeared in the proximity of the border of the halation 326 may be extracted erroneously as blood vessels. The shadow 327 refers to an area in which the pixel values are low relative to those of the surrounding pixels due to shortage of the illumination light caused by the relative relationship between the form 122 such as the protrusion on the object and the irradiation angle of the illumination light. In the case where the scale of the shadow 327 is at a similar level to that of the surface blood vessels 123 or the superficial blood vessels 124, the shadow 327 may be extracted erroneously as the blood vessels.

Figure 27:
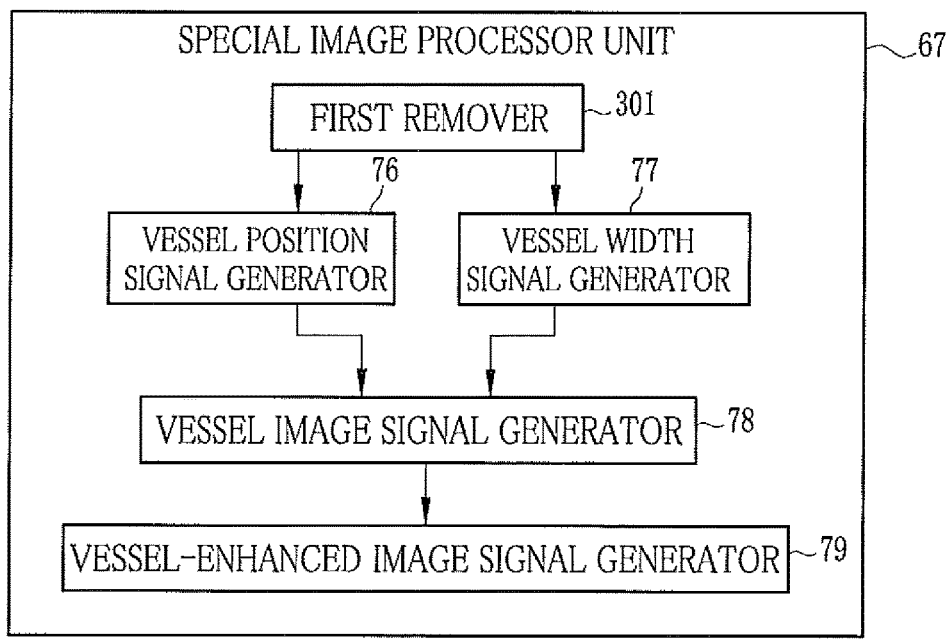
FIG. 27 is a block diagram illustrating functions of a special image processor according to a third embodiment.

As illustrated in FIG. 27, the special image processor unit 67 in the endoscope system of the third embodiment is provided with a first remover 301 (remover) for removing the artifact. Other than that, the configuration of the endoscope system is similar to that of the endoscope system 10 of the first embodiment or the endoscope system 200 of the second embodiment. The first remover 301 detects the artifact from the image signal received by the special image processor unit 67 from the image processing selector 61 and removes the artifact. The artifact includes the halation 326 and the noise that appears in the proximity of the halation 326 (hereinafter referred to as the halation and the like), the shadows 327, and the like. The vessel position signal generator 76 and the vessel width signal generator 77 generate the vessel position signal and the vessel width signal, respectively, from the image signal from which the artifact has been removed. Owing to the use of the image signal from which the artifact has been removed, the surface blood vessels 123 and the superficial blood vessels 124 are extracted accurately.

Figure 28:
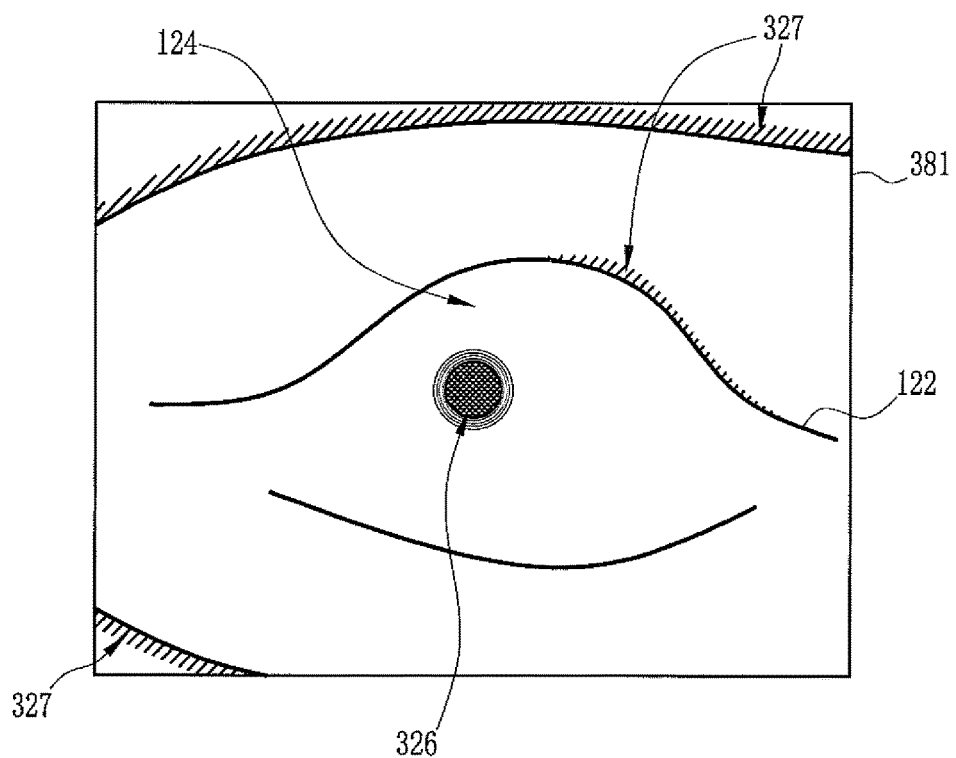
FIG. 28 is a schematic view illustrating an R image signal.

To detect the artifact, the first remover 301 uses, for example, the R image signal corresponding to the red wavelength range of the RGB image signals received by the special image processor unit 67. The contrast of the surface blood vessels 123 and the superficial blood vessels 124 is high in the B image signal corresponding to the blue wavelength range. The G image signal corresponding to the green wavelength range may include the blood vessels located in a position deeper than that of the surface blood vessels 123. As illustrated in FIG. 28, although an R image signal 381 displays the form 122 such as the protrusion on the object, the halation and the like, and the shadows 327, the R image signal 381 carries little information about the blood vessels. For this reason, the first remover 301 subtracts the R image signal from each of the B image signal (or the B1 image signal and the B2 image signal) and the G image signal to remove the artifact from each of the B image signal and the G image signal.

In the case where the halation and the like are removed as the artifact, note that the first remover 301 detects a region, in which a pixel value is greater than or equal to a specific threshold value, as the halation 326 and detects the pattern of alternating dark and bright lines in the proximity of the border of the halation 326. The first remover 301 may inhibit the vessel position signal generator 76 and the vessel width signal generator 77 to extract the blood vessels from the region in which the halation and the like are detected.

The first remover 301 uses the R image signal to remove the halation and the like and the shadows 327 at once, or by one operation. The removal of the halation and the like and the removal of the shadows 327 may be performed separately. For example, in the case where only the halation and the like are to be removed without consideration of the shadows 327, it is preferred to use the image signal that is used by the vessel position signal generator 76 and the vessel width signal generator 77, to detect and remove the halation and the like. The first remover 301 may use the B image signal (or the B1 image signal and the B2 image signal) or the G image signal that is used by the vessel position signal generator 76 and the vessel width signal generator 77, to detect and remove the halation and the like. Instead, the first remover 301 may use the R image signal to detect and remove the shadows 327 from the B image signal (or the B1 image signal and the B2 image signal) or the G image signal.

Figure 29:
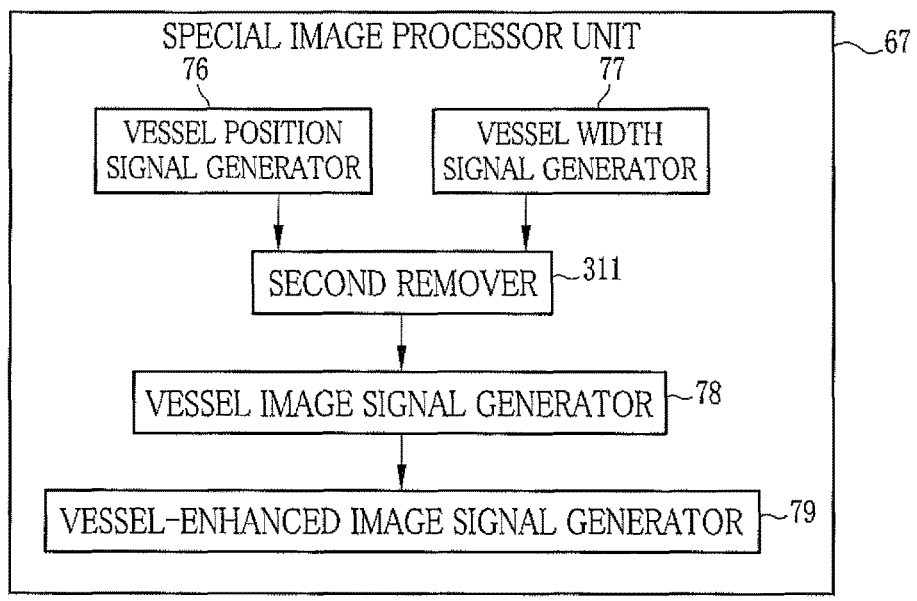
FIG. 29 is a block diagram illustrating functions of a special image processor of a modified example.

In the third embodiment, the artifact is removed from the image signal used by the vessel position signal generator 76 and the vessel width signal generator 77. The vessel position signal and the vessel width signal are generated from the image signal from which the artifact has been removed. Instead, the artifact (the noise due to the shadow 327 and the halation and the like) may be removed from the vessel position signal generated by the vessel position signal generator 76 and the vessel width signal generated by the vessel width signal generator 77. In this case, the special image processor unit 67 is provided with a second remover 311 (see FIG. 29). The second remover 311 removes the artifact or the noise due to the artifact from the vessel position signal generated by the vessel position signal generator 76. The second remover 311 also removes the artifact or the noise due to the artifact from the vessel width signal generated by the vessel width signal generator 77.

For example, the second remover 311 uses one of the RGB image signals inputted to the special image processor unit 67, to detect the halation and the like. The second remover 311 removes the blood vessels (that is, the noise due to the halation and the like) with a high possibility of erroneous extraction and extracted within a region in which the halation and the like has been detected, from the vessel position signal and the vessel width signal generated by the vessel position signal generator 76 and the vessel width signal generator 77. The second remover 311 uses, for example, the R image signal of the RGB image signals inputted to the special image processor unit 67, to detect a region corresponding to the shadow 327. The second remover 311 removes the blood vessels (that is, the noise due to the shadow 327) with a high possibility of erroneous extraction and extracted within a region in which the shadow 327 has been detected, from the vessel position signal and the vessel width signal generated by the vessel position signal generator 76 and the vessel width signal generator 77.

The second remover 311 inputs the vessel position signal and the vessel width signal from each of which the artifact has been removed to the vessel image signal generator 78. The vessel image signal generator 78 generates the vessel image signal from the vessel position signal and the vessel width signal from each of which the artifact has been removed. By removing the artifact from each of the vessel position signal and the vessel width signal that include the artifact, the surface blood vessels 123 and the superficial blood vessels 124 are extracted accurately, as in the case of second embodiment.

In the third embodiment, the halation and the like and the shadows 327, and/or the noise due to the halation and the shadows 327 are removed. In addition, glandular and ductal structure (pit pattern) may become the artifact in extracting the blood vessels. For example, the glandular and ductal structure appears as streaks of high luminance in the image signal. An area between the streaks of the glandular and ductal structure has luminance lower than that of the glandular and ductal structure. A low luminance area between the streaks of the glandular and ductal structure may be extracted erroneously as the blood vessels. In the case where the first remover 301 (see FIG. 27) is provided, it is preferred that the first remover 301 uses, for example, the B image signal (or the B1 image signal and the B2 image signal) of the RGB image signals inputted to the special image processor unit 67, to detect the glandular and ductal structure, being the streak-shaped high luminance area, and remove the image of the glandular and ductal structure from the image signal to be used by the vessel position signal generator 76 and the vessel width signal generator 77. Thereby the erroneous extraction of the low luminance area located between the streaks of the glandular and ductal structure is prevented at the time of generating the vessel position signal and the vessel width signal. The first remover 301 may eliminate the region in which the glandular and ductal structure has been detected, from a region from which the blood vessels are to be detected. Thereby the erroneous detection of the blood vessels in the vessel position signal and the vessel width signal is prevented.

In the case where the second remover 311 (see FIG. 29) is provided to remove the artifact or the noise due to the artifact from each of the vessel position signal and the vessel width signal, the second remover 311 uses one of the RGB image signals inputted to the special image processor unit 67, to detect a region in which the glandular and ductal structure is included. It is preferred that the second remover 311 removes the blood vessels extracted within the region corresponding to the detected glandular and ductal structure, from each of the vessel position signal and the vessel width signal. Thereby the blood vessels that are erroneously extracted due to the presence of the glandular and ductal structure are removed from each of the vessel position signal and the vessel width signal.

Note that, in the case where the endoscope system 300 of the third embodiment extracts the blood vessels located at a specific depth, as in the case of second embodiment, and the artifact or a noise component due to the artifact is removed with the use of the R image signal corresponding to the red wavelength range, the V-LED 23a and the R-LED 23d are turned on in the first emission mode. It is preferred to image the object irradiated with the illumination light that includes the violet light V and the red light R to generate the B1 image signal and an R image signal (hereinafter referred to as the R1 image signal) corresponding to the red wavelength range. The R1 image signal is used to remove the artifact from the B1 image signal. In the case where the artifact is removed from the B2 image signal or the G image signal that are generated by imaging the object irradiated with the illumination light of the second emission mode, an R image signal (R2 image signal) corresponding to the red light included in the illumination light of the second emission mode is used to remove the artifact. Thus, the accuracy in removing the artifact is improved by using the image signals generated at the same time by imaging the object.

[Fourth Embodiment]

In the first to third embodiments, the vessel image signal generator 78 of the special image processor unit 67 generates the vessel image signal 151 or 251. Then the vessel-enhanced image signal generator 79 of the special image processor unit 67 superimposes the vessel image signal 151 or 251 onto the base image signal to generate the vessel-enhanced image signal 161 or 261. Instead of or in addition to generating the vessel-enhanced image signal 161 or 261, the vessel image signal 151 or 251 may be used to obtain the information about the blood vessels that is an indicator of the diagnosis. "The information about the blood vessels that is the indicator of the diagnosis" refers to the density of the blood vessels (hereinafter referred to as the blood vessel density), the presence or absence or the percentage of the blood vessels of abnormal shapes, the number of the blood vessels in a unit area, the running direction of the blood vessels, the variations in the running directions of the blood vessels (the uniformity in the directions of the blood vessels), or the like.

Figure 30:
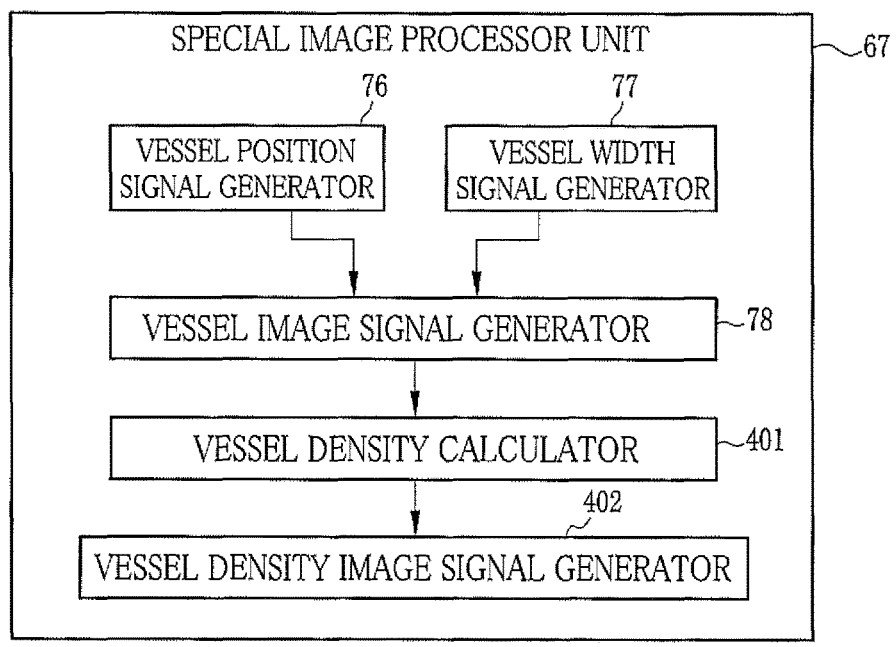
FIG. 30 is a block diagram illustrating functions of a special image processor of a fourth embodiment.

For example, in the case where the blood vessel density is calculated as the information about the blood vessels that is the indicator of the diagnosis, the special image processor unit 67 is provided with a vessel density calculator 401 and a vessel density image signal generator 402 (see FIG. 30). The vessel density calculator 401 uses the vessel image signal 151 or 251, which is generated by vessel image signal generator 78, or an image generated from the vessel image signal 151 or 251 to calculate the blood vessel density. The blood vessel density is a percentage of the blood vessels in a unit area. The vessel density calculator 401 calculates the blood vessel density on a pixel-by-pixel basis. To be more specific, a region of a specific size (unit area) including, at its center, the pixel in which the blood vessel density is to be calculated is cut out from the vessel image signal 151 or 251. Then the percentage of the surface blood vessels 123 and the superficial blood vessels 124 in all of the pixels within the region is calculated. This calculation is performed for every pixel in the vessel image signal 151 or 251. Thus, the blood vessel density in each pixel in the vessel image signal 151 or 251 is calculated.

Figure 31:
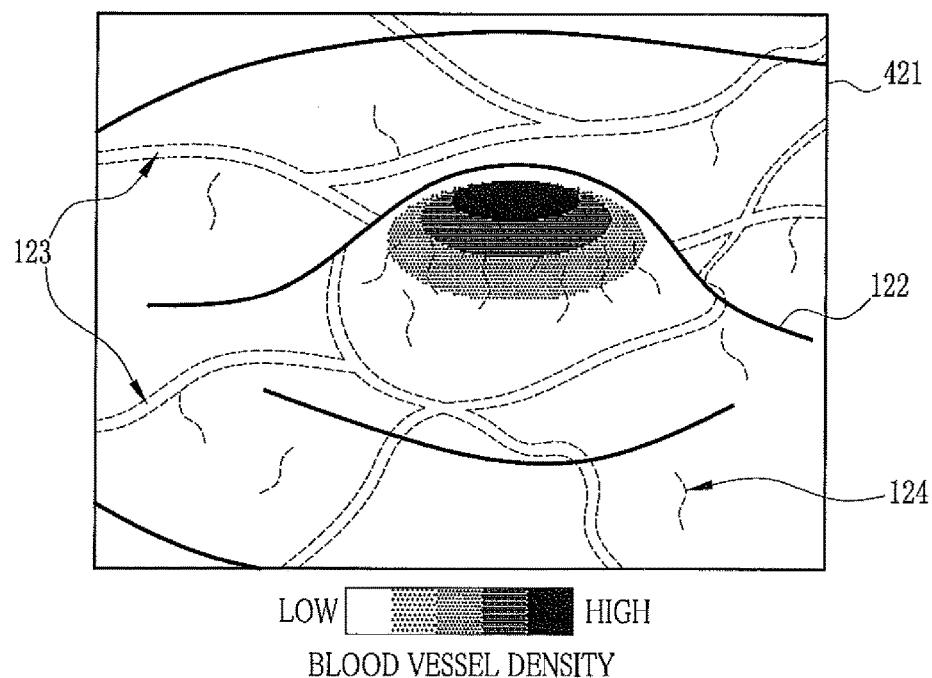
FIG. 31 is a schematic view illustrating a vessel density image signal.

As illustrated in FIG. 31, the vessel density image signal generator 402 generates a vessel density image signal 421. The vessel density image signal 421 is an image signal in which each pixel of the base image signal, which is generated in a manner similar to the vessel-enhanced image signal generator 79, is colored in accordance with the value of the blood vessel density. Thus, the vessel density image signal 421 represents the blood vessel density with color temperature.

As described above, because the endoscope system uses the vessel image signal 151 or 251, in which the position and the widths of the blood vessels are extracted accurately, to calculate the blood vessel density or the like that is the indicator of the diagnosis, the indicator calculated is more accurate and more useful than that calculated by the conventional endoscope system. The endoscope system allows the accurate calculation of the value that has been inadequate for the indicator of the diagnosis due to its inaccuracy, and the use thereof as the indicator of the diagnosis.

In the fourth embodiment, the vessel image signal 151 or 251 is used to calculate the blood vessel density for each pixel and the vessel density image signal 421, which represents the blood vessel density in colors, is generated. In the case where one blood vessel density is calculated for the entire vessel image signal 151 or 251, in other words, in the case where the unit area is the entire vessel image signal 151 or 251, the value of the blood vessel density may be outputted together with the base image signal or the vessel-enhanced image signal 161 or 261 to the monitor 18. In the case where the blood vessel density is calculated for each pixel as described above, the base image signal or the vessel-enhanced image signal 161 or 261 may be displayed on the monitor 18 and the value of the blood vessel density of an area designated on the monitor 18 may be outputted to the monitor 18.

In the first embodiment, each of the vessel position signal generator 76 and the vessel width signal generator 77 performs the black top-hat transform. Note that, in the case where the image signal is inverted into an image signal in which the blood vessels are displayed at high luminance (white color), the white top-hat transform is performed instead of the black top-hat transform. In the second embodiment, the vessel position signal generator 76 performs the white top-hat transform. In the case where the image signal is inverted into an image signal in which the blood vessels are displayed at low luminance (black color), the black top-hat transform may be performed instead of the white top-hat transform, in a like manner.

In the first to fourth embodiments, the black top-hat transform or the white top-hat transform is used to generate the vessel position signal and the vessel width signal. It is preferred that the structuring element used for the black top-hat transform and the white top-hat transform has a rhombus shape. The structuring element may have a circular shape because the direction in which the blood vessel runs may be at any degree within 360 degrees. In the case where the running direction of the blood vessels is determined in advance by using a Gabor filter or the like, the structure element having a shape suitable for the running direction of the blood vessels may be used.

In the first to fourth embodiments, the black top-hat transform or the white top-hat transform is used to generate the vessel position signal. Instead, template matching, the Gabor filter, a thresholding method, a machine learning method or the like may be used. The template matching is the processing to extract a shape that matches a template prepared in advance. For example, the template corresponds to the blood vessels. In the case where the template matching is used to generate the vessel position signal, only the specific blood vessels (for example, the blood vessels with an abnormal shape that is highly related to a lesion) may be extracted instead of extracting all the blood vessels. In the case where the template matching is used to extract the specific blood vessels, the monitor 18 may display the information for assisting the diagnosis, based on the features of the blood vessels extracted. For example, the monitor 18 displays "there is a possibility of a lesion CC" in the case where the blood vessels of a type BB in a category AA are extracted.

The Gabor filter extracts a structure having a specific direction. In the case where the Gabor filter is used to generate the vessel position signal, the blood vessels are extracted using the Gabor filter in vertical, horizontal, and diagonal directions. The Gabor filter is used to determine whether the running directions of the blood vessels are uneven (unbalanced). For example, in the case where all of the components in the vertical, horizontal, and diagonal directions are uniform, it is preferred to display a message or the like, on the monitor 18, displaying that there is a possibility of irregularly running blood vessels, to assist the diagnosis.

A thresholding method is to set a specific threshold value and to extract an area with the pixel values less than or equal to the threshold value as blood vessels. In the case where the vessel position signal is generated by using the thresholding method instead of the black top-hat transform and there is unevenness in the amount of illumination light applied, it is preferred to perform a process to cancel out the unevenness. For example, the unevenness in the amount of the illumination light is cancelled out by the normalization using a low frequency component or the R image signal, in which almost no blood vessels are displayed (included) because there is virtually no absorption by hemoglobin. In the case where the thresholding method is used, a threshold value may be determined dynamically. For example, Otsu's method may be used.

In the first to fourth embodiments, the vessel width signal is generated using the LoG filter. Instead, the vessel width signal may be generated using only the Laplacian filter. However, it is preferred to use the LoG filter in combination with the Gaussian filter to improve the robustness against noise. In a case where the LoG filter is used, the image signal, being smoothed by the Gaussian filter, includes a blur. It is preferred to perform morphological operations on the image signal that has been subjected to the LoG filtering to correct the blur caused by the Gaussian filter.

In the first to fourth embodiments, it is assumed that the blur of the blood vessels takes a Gaussian function shape. It may be assumed that the blur of the blood vessels may take another shape other than the Gaussian function shape. In this case, the vessel width signal may be generated using a filter that solves the border between the blood vessels and the mucosa in the width direction of the blood vessels as an analysis solution, instead of the LoG filter. The border between the mucosa and the blood vessels may be, for example, a full width at half maximum of a peak value or the point at which the peak value is attenuated to a specific percentage "X %", at which the inclination is most steep.

In the first to fourth embodiments, it is estimated that the blur of the blood vessels in the image signal has a Gaussian function shape. In the strict sense, the blur of the blood vessels varies with the state of the mucosa, the blood vessel depth, and the like. Therefore it is preferred to correct the vessel width signal through estimating the state of the mucosa, the blood vessel depth, and the like based on the image.

In the first to fourth embodiments, the light source unit 20 comprises the LEDs 23a to 23d of four colors. Instead, a laser, a xenon lamp, or the like may be used. The light source unit 20, which may or may not be LEDs, may be used in combination with any optical filter for limiting a wavelength range. The optical filter may be provided on the incident surface of the image sensor 48.

In the first to fourth embodiments, the vessel position signal and the vessel width signal are generated from the image signal received from the image processing selector 61. Instead, the vessel position signal and the vessel width signal may be generated from the image signal after the noise removal process, which improves the accuracy in extracting the blood vessels. In particular, in generating the vessel position signal 231 in the second embodiment, it is preferred to perform white top-hat filtering after the noise removal process is performed on the differential image signal. It is preferred to use a smoothed filter or a Gaussian filter for the noise removal process performed before the vessel position signal and the vessel width signal are generated. In the case there are two or more image signals, the noise removal process may be performed on the arithmetic mean of the successively generated image signals.

In the first to fourth embodiments, the vessel-enhanced image signal generator 79 generates the base image signal of the same white color as that of the normal image and superimposes the vessel image signal 151 or 251 onto the base image signal to generate the vessel-enhanced image signal 161 or 261. Instead, the base image signal of the coloration to enhance the blood vessels may be generated by assigning the original B image signal (or the original B1 image signal or the original B2 image signal) to the blue color or the green color of the image signal to be outputted and by assigning the original G image signal to the red color of the image signal to be outputted, or like. The enhanced blood vessel image may be generated by superimposing the vessel image signal onto the base image signal in which the blood vessels have been enhanced. In this case, in the second emission mode of the second embodiment, only the B-LED 23b is turned on and only the blue light B is used as the illumination light. Thereby the green light G and the red light R are eliminated from the B2 image signal and the blood vessel contrast of the blue light B is increased (see FIG. 17). The intersection of the graph of the blood vessel contrast obtained by using the blue light B and the graph of the blood vessel contrast obtained by using the violet light V shifts to a shallower position under the mucosal surface. Thus the information of the superficial blood vessels in close proximity to the surface of the mucosa is obtained by using the differential image signal, being the difference between the B1 image signal and the B2 image signal, which have been subjected to the log conversion.

In the first to fourth embodiments, the position and the widths of a blood vessels are displayed as an image. In a case where an imaging distance (a distance between the image sensor 48 and the object) is obtained, the widths of the blood vessels are calculated based on the number of pixels in the image signal and the imaging distance. The average width of the blood vessels present in the vessel image signal is displayed in a numeric value on the monitor 18. The width of the blood vessel designated on the monitor 18 may be displayed in a numeric value. The imaging distance may be measured using a laser interferometer. The imaging distance may be estimated based on the distribution of frequency components in the image signal.

In the first to fourth embodiments, the vessel-enhanced image signal or the like is displayed on the monitor 18 in real time. The vessel-enhanced image signal or the like may be generated, in a manner similar to those of the above embodiment, from an image signal stored in an external storage device (not shown) of the endoscope system 10. In the case where the vessel position signal, the vessel width signal, and the vessel-enhanced image signal are displayed in real time as described in the first to fourth embodiments, two or more image signals with different resolutions may be generated from the image signal received from the image processing selector 61 and then the vessel position signal and the vessel width signal may be generated for each of the image signals with the different resolutions, to improve process speed.

For example, in the first embodiment, the vessel position signal generator 76 and the vessel width signal generator 77 generate a first resolution image signal, from which the surface blood vessels 123 are likely to be extracted, and a second resolution image signal, from which the superficial blood vessels 124 are likely to be extracted, from the image signal obtained from the image processing selector 61. Then the vessel position signal generator 76 and the vessel width signal generator 77 generate the first vessel position signal and the first vessel width signal that represent the surface blood vessels 123 from the first resolution image signal, and the second vessel position signal and the second vessel width signal that represent the superficial blood vessel 124 from the second resolution image signal. Thereafter, the vessel position signal generator 76 and the vessel width signal generator 77 generate the first vessel image signal that represents the surface blood vessels 123 from the first vessel position signal and the first vessel width signal, and the second vessel image signal that represents the superficial blood vessel 124 from the second vessel position signal and the second vessel width signal. The vessel-enhanced image signal generator 79 superimposes the first vessel image signal and the second vessel image signal onto the base image signal to generate the vessel-enhanced image signal similar to those of the above embodiments.

Figure 32:
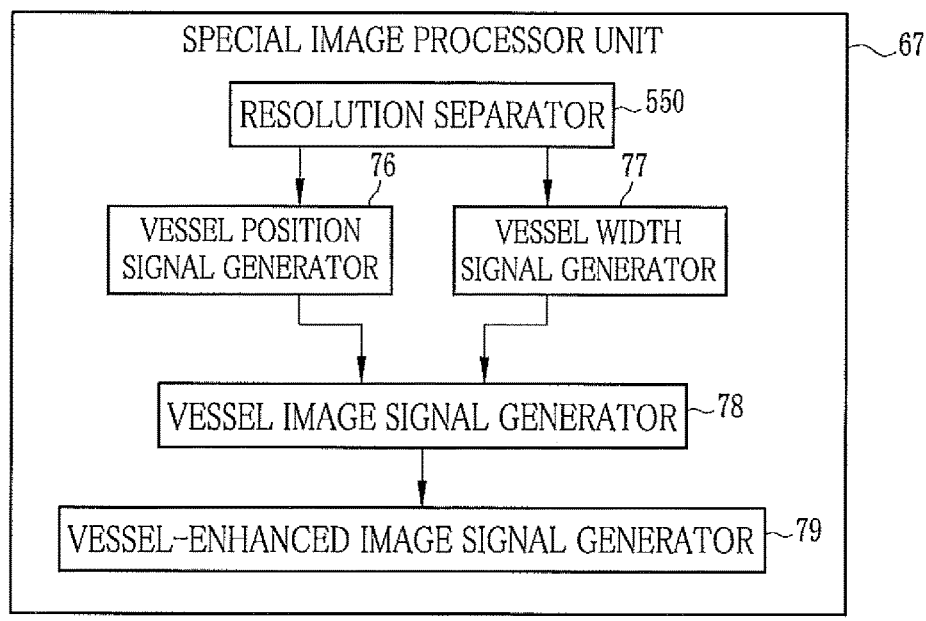
FIG. 32 is a block diagram illustrating a special image processor comprising a resolution separator.

In the second embodiment, as illustrated in FIG. 32, the special image processor unit 67 comprises a resolution separator 550. The resolution separator 550 separates each of the B1 image signal and the B2 image signal into two or more image signals with different resolutions. For example, the resolution separator 550 generates a first resolution B1 image signal and a first resolution B2 image signal, which have a first resolution, and a second resolution B1 image signal and a second resolution B2 image signal, which have a second resolution different from the first resolution, from the B1 image signal and the B2 image signal.

The vessel position signal generator 76 and the vessel width signal generator 77 generate the vessel position signal and the vessel width signal, respectively, for each of the different resolutions. To be more specific, the vessel position signal generator 76 and the vessel width signal generator 77 generate the first vessel position signal and the first vessel width signal from the first resolution B1 image signal and the first resolution B2 image signal, and generates the second vessel position signal and the second vessel width signal from the second resolution B1 image signal and the second resolution B2 image signal. Thereafter, the vessel image signal generator 78 generates the first vessel image signal from the first vessel position signal and the first vessel width signal, and the second vessel image signal from the second vessel position signal and the second vessel width signal. The vessel-enhanced image signal generator 79 adjusts the resolutions of the first and second vessel image signals with the resolution of the base image and then superimposes the first and second vessel image signals onto the base image signal to generate the vessel-enhanced image signal similar to those of the above embodiments.

As described above, in the case where the blood vessels are extracted by separating the resolution into two or more levels of resolutions, the size of the structuring element used for the morphological operations is reduced. Thereby the processing load of the processor device 16 is reduced. There may be cases where the blood vessels with different widths are located at substantially the same depth under the mucosal surface. In the case where the blood vessels are extracted by separating the resolution into two or more levels of resolution as described above, each of the blood vessels with different widths located at substantially the same depth under the mucosal surface is extracted reliably.

Note that the vessel image signal generator 78 may adjust the resolution of the first vessel image signal with the resolution of the second vessel image signal and then combine the first vessel image signal with the second vessel image signal, thereby generating a composite vessel image signal. In this case, the vessel-enhanced image signal generator 79 adjusts the resolution of the composite vessel image signal with the resolution of the base image signal and then superimposes the composite vessel image signal onto the base image signal, thereby generating the vessel-enhanced image signal 161 or 261.

Figure 33:
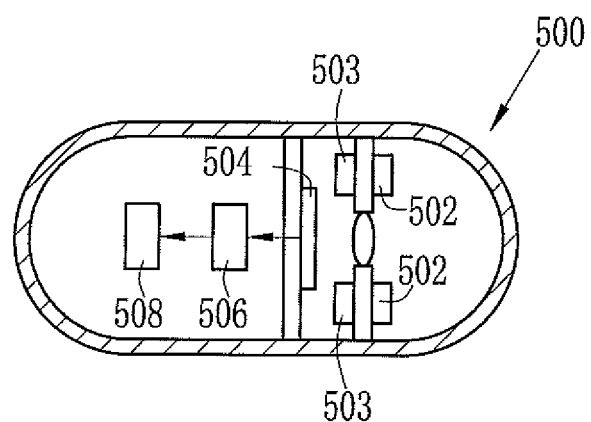
FIG. 33 is a schematic view illustrating a capsule endoscope.

Note that, in the first to fourth embodiments, the implementation of the present invention is performed by using one of the endoscope systems 10, 200, and 300, each of which comprises the endoscope 12 provided with the image sensor 48. The observation is performed by inserting the endoscope 12 in a body cavity. The present invention is also suitable for a capsule endoscope system. For example, as illustrated in FIG. 33, the capsule endoscope system comprises at least a capsule endoscope 500 and a processor device (not shown).

The capsule endoscope 500 comprises a light source unit 502, a light source controller 503, an image sensor 504, a signal processor 506, and a transmission/reception antenna 508. The light source unit 502 is similar to the light source unit 20 described in the above embodiments. The light source controller 503 drives the light source unit 502 in a manner similar to the light source controller 22 of the above embodiments. The light source controller 503 communicates with the processor device of the capsule endoscope system through the transmission/reception antenna 508. The processor device of the capsule endoscope system is substantially similar to the processor device 16 of the above embodiments except that the signal processor 506 has functions of the normal image processor unit 66 and the special image processor unit 67. The vessel-enhanced image signal and the like generated by the signal processor 506 are transmitted to the processor device through the transmission/reception antenna 508. The image sensor 504 is similar to the image sensor 48 of the above embodiments.

Various changes and modifications are possible in the present invention and may be understood to be within the present invention.

What is claimed is:

1. An endoscope system comprising:
   a light source unit for generating illumination light;
   an image sensor for imaging an object of interest irradiated with the illumination light; and
   an electric signal processor device configured to:
   obtain an image signal from the image sensor, the image signal representing the object;
   generate a vessel position signal from the image signal, the vessel position signal representing a position of a blood vessel of the object;
   generate a vessel width signal from the image signal, the vessel width signal representing a width of the blood vessel; and
   generate a vessel image signal from the vessel position signal and the vessel width signal, the vessel image signal representing the blood vessel,
   wherein the vessel position signal and the vessel width signal are used to extract the blood vessel located in the position represented by the vessel position signal and having the width represented by the vessel width signal, to generate the vessel image signal,
   wherein an AND of the vessel width signal and the vessel position signal is calculated to generate the vessel image signal, and
   wherein pixels that have specific positive values in both of the vessel position signal and the vessel width signal are extracted in the calculation of the AND.

2. The endoscope system according to claim 1, wherein the electric signal processor device obtains a first image signal as the image signal from the image sensor, the first image signal corresponding to first illumination light of the illumination light, and the electric signal processor device obtains a second image signal as the image signal from the image sensor, the second image signal corresponding to second illumination light that differs in wavelength range or optical spectrum from the first illumination light, and the electric signal processor device generates the vessel position signal from the first image signal and the second image signal, the vessel position signal representing the position of the blood vessel of the object, and the electric signal processor device generates the vessel width signal from the first image signal or the second image signal, the vessel width signal representing the width of the blood vessel of the object.

3. The endoscope system according to claim 2, wherein the electric signal processor device is further configured to correct at least one of the first image signal and the second image signal and for performing registration between the object represented by the first image signal and the object represented by the second image signal, wherein the electric signal processor device generates the vessel position signal from the first and second image signals on which the registration of the objects has been performed by the electric signal processor device, and the electric signal processor device generates the vessel width signal from the first or second image signal on which the registration has been performed by the electric signal processor device.

4. The endoscope system according to claim 2, wherein the electric signal processor device is further configured to correct at least one of the first image signal and the second image signal and for setting a ratio between brightness of the first image signal and brightness of the second image signal to a specific ratio, wherein the electric signal processor device generates the vessel position signal from the first and second image signals in which the brightness has been adjusted by the electric signal processor device, and the electric signal processor device generates the vessel width signal from the first or second image signal in which the brightness has been adjusted by the electric signal processor device.

5. The endoscope system according to claim 1, wherein the electric signal processor device performs second-order differentiation on the image signal and generates the vessel width signal based on zero-crossing points of the image signal that has been subjected to the second-order differentiation.

6. The endoscope system according to claim 5, wherein the electric signal processor device removes noise from the first image signal or the second image signal and performs the second-order differentiation on the first or second image signal from which the noise has been removed.

7. The endoscope system according to claim 1, wherein the electric signal processor device performs a morphological operation on the image signal to generate the blood vessel position signal.

8. The endoscope system according to claim 1, wherein the electric signal processor device is further configured to remove a shadow or halation from the image signal, the shadow or halation occurring due to the illumination light, wherein the electric signal processor device generates the vessel position signal from the image signal from which the shadow or the halation has been removed, and the electric signal processor device generates the vessel width signal from the image signal from which the shadow or the halation has been removed.

9. The endoscope system according to claim 8, wherein the electric signal processor device uses a red image signal to remove the shadow from the image signal, the red image signal corresponding to light in a red wavelength range of the illumination light.

10. The endoscope system according to claim 1, wherein the electric signal processor device removes noise that occurred due to a shadow or halation from the vessel position signal and for removing noise that occurred due to the shadow or the halation from the vessel width signal.

11. The endoscope system according to claim 10, wherein the electric signal processor device uses the image signal corresponding to a red wavelength range to remove the noise that occurred due to the shadow.

12. The endoscope system according to claim 1, wherein the electric signal processor device is further configured to calculate blood vessel density with the use of the vessel image signal or an image generated by using the vessel image signal.

13. The endoscope system according to claim 12, wherein the electric signal processor device is further configured to generate a vessel density image signal with the use of the blood vessel density, the vessel density image signal representing the blood vessel density.

14. The endoscope system according to claim 1, wherein an image is generated by superimposing the vessel image signal onto an image generated from the image signal.

15. The endoscope system according to claim 1, wherein the electric signal processor device is further configured to separate the image signal into two or more image signals having different resolutions, wherein the electric signal processor device generates the vessel position signal for each of the resolutions, and the electric signal processor device generates the vessel width signal for each of the resolutions, and the electric signal processor device uses the vessel position signal and the vessel width signal that have been generated for each of the resolutions to generate the vessel image signal for each of the resolutions.

16. A processor device comprising:

an electric signal processor device configured to:

obtain an image signal representing an object of interest;

generate a vessel position signal from the image signal, the vessel position signal representing a position of a blood vessel of the object;

generate a vessel width signal from the image signal, the vessel width signal representing a width of the blood vessel; and generate a vessel image signal from the vessel position signal and the vessel width signal, the vessel image signal representing the blood vessel, wherein the vessel position signal and the vessel width signal are used to extract the blood vessel located in the position represented by the vessel position signal and having the width represented by the vessel width signal, to generate the vessel image signal, wherein an AND of the vessel width signal and the vessel position signal is calculated to generate the vessel image signal, and wherein pixels that have specific positive values in both of the vessel position signal and the vessel width signal are extracted in the calculation of the AND.

17. A method for operating an endoscope system comprising the steps of:

generating illumination light with a light source unit;

imaging an object of interest irradiated with the illumination light, with an image sensor;

obtaining an image signal representing the object from the image sensor, with an image signal obtaining section;

generating a vessel position signal representing a position of a blood vessel of the object from the image signal, with an electric signal processor device;

generating a vessel width signal representing a width of the blood vessel of the object from the image signal, with the electric signal processor device; and generating a vessel image signal representing the blood vessel from the vessel position signal and the vessel width signal, with the electric signal processor device, wherein the vessel position signal and the vessel width signal are used to extract the blood vessel located in the position represented by the vessel position signal and having the width represented by the vessel width signal, to generate the vessel image signal, wherein an AND of the vessel width signal and the vessel position signal is calculated to generate the vessel image signal, and wherein pixels that have specific positive values in both of the vessel position signal and the vessel width signal are extracted in the calculation of the AND.

* * * * *